US012285233B2

United States Patent
Zhu et al.

(10) Patent No.: US 12,285,233 B2
(45) Date of Patent: Apr. 29, 2025

(54) NON-FIBER FLAT-PANEL BREAST DIFFUSION OPTICAL TOMOGRAPHY SYSTEM

(71) Applicant: Xidian University, Xi'an (CN)

(72) Inventors: Shouping Zhu, Xi'an (CN); Xu Cao, Xi'an (CN); Yihan Wang, Xi'an (CN); Xueli Chen, Xi'an (CN); Fanzhen Meng, Xi'an (CN); Duofang Chen, Xi'an (CN); Jing Zhao, Xi'an (CN)

(73) Assignee: XIDIAN UNIVERSITY, Xi'an (CN)

( * ) Notice: Subject to any disclaimer, the term of this patent is extended or adjusted under 35 U.S.C. 154(b) by 678 days.

(21) Appl. No.: 17/511,089

(22) Filed: Oct. 26, 2021

(65) Prior Publication Data

US 2022/0047161 A1 Feb. 17, 2022

Related U.S. Application Data

(63) Continuation of application No. PCT/CN2020/138604, filed on Dec. 23, 2020.

(30) Foreign Application Priority Data

| Jan. 13, 2020 | (CN) | 202010032176.0 |
| Mar. 12, 2020 | (CN) | 202010171553.9 |
| Apr. 3, 2020 | (CN) | 202010261131.0 |

(51) Int. Cl.
A61B 5/00 (2006.01)

(52) U.S. Cl.
CPC .......... *A61B 5/0013* (2013.01); *A61B 5/0066* (2013.01); *A61B 5/0073* (2013.01);
(Continued)

(58) Field of Classification Search
CPC ... A61B 5/0013; A61B 5/0066; A61B 5/0073; A61B 5/0086; A61B 5/0091; A61B 5/708; G06T 3/40; G06T 7/00
See application file for complete search history.

(56) References Cited

U.S. PATENT DOCUMENTS

| 7,804,070 B1 * | 9/2010 | Pan ..................... A61B 5/0091 |
| | | 250/341.1 |
| 9,833,147 B2 * | 12/2017 | Suzuki ................ A61B 8/0825 |

(Continued)

FOREIGN PATENT DOCUMENTS

| CN | 107822618 A | 3/2018 |
| CN | 110123281 A | 8/2019 |

(Continued)

OTHER PUBLICATIONS

Ruzairi Abdul Rahim, Mohd Hafiz Fazalul Rahiman, Leong Lai Chen, Chan Kok San and Pang Jon Fea, Hardware Implementation of Multiple Fan Beam Projection Technique in Optical Fibre Process Tomography, May 23, 2008, Sensors 2008, 8, 3406-3428 (Year: 2008).*

(Continued)

*Primary Examiner* — Michelle M Iacoletti
*Assistant Examiner* — Maher Yazback
(74) *Attorney, Agent, or Firm* — WPAT, PC

(57) ABSTRACT

A breast diffusion optical tomography (DOT) device includes a light source, a detector, a mechanical driver and a contour acquisitor without using optical fiber and reduce the system complexity. The light source includes M1 number of multi-wavelength near-infrared light emitters for a continuous-wave mode and M2 number of laser diodes of different wavelengths for a frequency-domain mode. The detector includes N1 number of silicon photomultipliers for detecting near-infrared light in the continuous-wave mode and N2 number of silicon photomultipliers for detecting near-infrared light in the frequency-domain mode. The mechanical driver adjusts a distance between the light source and the detector. The contour acquisitor obtains the geometry of a patient's breast for reconstruction. The DOT device uses amplitude and phase information obtained in the (Continued)

frequency-domain mode to estimate initial optical parameters of tissues and then apply for reconstruction in the continuous-wave mode.

20 Claims, 20 Drawing Sheets

(52) U.S. Cl.
CPC .......... *A61B 5/0086* (2013.01); *A61B 5/0091* (2013.01); *A61B 5/708* (2013.01)

(56) References Cited

U.S. PATENT DOCUMENTS

| | | | | |
|---|---|---|---|---|
| 2008/0292164 | A1* | 11/2008 | Azar | G06T 7/0012 382/131 |
| 2009/0240139 | A1* | 9/2009 | Yi | A61B 5/0073 600/425 |
| 2013/0109963 | A1* | 5/2013 | Zhu | A61B 5/7235 600/427 |
| 2013/0169759 | A1* | 7/2013 | Godavarty | G06T 17/20 348/47 |
| 2014/0160540 | A1* | 6/2014 | Hoshino | G02B 5/3016 359/2 |
| 2016/0278715 | A1* | 9/2016 | Yu | G06F 30/00 |
| 2018/0014733 | A1* | 1/2018 | Suwa | A61B 5/704 |
| 2019/0072897 | A1* | 3/2019 | Jepsen | G02B 26/128 |
| 2020/0008682 | A1 | 1/2020 | Dutta | |
| 2020/0107756 | A1* | 4/2020 | El Naqa | A61B 5/0059 |
| 2020/0116630 | A1* | 4/2020 | Zhu | G01N 21/474 |

FOREIGN PATENT DOCUMENTS

| | | | | |
|---|---|---|---|---|
| CN | 115067883 A | * | 9/2022 | A61B 5/004 |
| KR | 20160147102 A | | 12/2016 | |

OTHER PUBLICATIONS

He Jie, "A multi-wavelength continuous-wavefunctional near-infrared spectroscopy system using lock-in photon-countingtechnique", Apr. 15, 2019, pp. 1-80.

* cited by examiner

NON-FIBER FLAT-PANEL BREAST DIFFUSION OPTICAL TOMOGRAPHY SYSTEM

FIELD OF THE DISCLOSURE

The disclosure relates to the field of breast imaging technologies, and more particularly to a breast diffusion optical tomography device, a diffusion optical tomography system and a method for obtaining a breast surface contour.

BACKGROUND OF THE DISCLOSURE

Breast cancer ranks first in the incidence rate of female malignant tumors. Compared with other conventional imaging detection modalities for breast cancer, optics has advantages such as no ionizing radiation and low cost. Diffusion optical tomography (DOT) can realize a noninvasive three-dimensional functional information such as an endogenous hemoglobin concentration and a blood oxygen saturation. DOT has specificity for a detection of tumor targets, and has the potential for development and application in a field of breast cancer diagnosis.

At present, there are mainly two ways to implement DOT. In one way shown in FIG. 1, the patient needs to lie prone on a bed, and the breast is placed into an imaging cavity. The imaging cavity is filled with a matching solution, and a laser diode (LD) generates excitation light transmitted to a light source plate (source plane) through an optical fiber. Part of the light output from breast tissues is captured to a frequency domain (FD) detector through an optical fiber, and the rest of the light is captured by a charge-coupled device (CCD). In the other of the two ways, a light source as used is similar to the scheme provided in FIG. 1 and optical fibers are also used for optical signal transmission, but a detector thereof is to use a photomultiplier tube (PMT).

Firstly, the above-described ways both use the optical fibers for optical signal transmission, which increases the complexity of a system. At the same time, the optical fibers attenuate the optical signals greatly, and attenuation degrees of optical signals by different optical fibers vary greatly. Secondly, in the aspect of light detection, PMT or CCD is used at present, which results in a high cost of the system. Finally, the breast will deform after being squeezed by the plate-shaped structure. In the related art, a method for obtaining morphological features of the breast is mainly to put the breast into the imaging cavity filled with the matching solution, which would cause the system structure to be complex and reduce the comfort of patients.

There are three measurement methods for DOT technologies, including continuous-wave, time-domain and frequency-domain. As shown in FIG. 1, in a continuous-wave mode, the light source is usually constant, but sometimes it is modulated with low frequency to thereby improve the signal-noise ratio (SNR), and the absorption coefficient is reconstructed by calculating an amplitude attenuation of the output light. In a time-domain mode, the light source is an ultrashort pulse, and the absorption coefficient and scattering coefficient can be reconstructed by the broadening and amplitude attenuation of the output light in the time domain. In a frequency-domain mode, the light source is a sine wave of tens to hundreds of MHz, and the absorption and scattering coefficients are reconstructed by a phase delay and the amplitude attenuation of the output light. Due to a high cost of a time-domain mode system, more researches have been made on continuous-wave systems and frequency-domain systems.

In a continuous-wave mode, because the optical signal is weak, which is at the level of noise in the measurement. In addition, dark currents existed in components themselves and the ambient light would also cause some influences. In order to solve such problems, a low-frequency modulation method can be used to improve the signal-noise ratio.

In the frequency-domain mode, the light source is applied with a high-frequency modulation, and the absorption and the scattering coefficients are reconstructed by calculating the phase delay and signal attenuation between the output light and incident light.

In the DOT imaging, a boundary shape of breast tends to be irregular, and the distribution of optical parameters is not uniform, so it is almost impossible to obtain an analytical solution, and therefore a numerical method is used to obtain an approximate solution. There are two kinds of numerical methods commonly used, including a finite difference method (FDM) and a finite element method (FEM). The finite difference method uses a difference quotient to approximate differential, and thereby solving differential equations. The finite element method transforms a partial differential equation into an integral equation firstly, then discretizes the integral equation in a solution area to obtain a finite element equation, and finally obtains an approximate solution of a partial differential equation by solving the finite element equation. Compared with the finite difference method, the advantage of the finite element method is that it can flexibly deal with the solution area of irregular shapes, so the finite element method is often used to solve the problem. In a process of DOT image reconstruction, an accuracy of a mesh morphology of a target area and an accuracy of mapping representations of "source" and "detected" positions in the mesh are very important for a final realization of quantification of internal optical parameters of the breast tissues when using the finite element method for an optical modeling and a reverse problem solving. There are two conventional methods to obtain morphological features for modeling. The first method is to put tissues to be measured into the imaging cavity with a moderate size and a regular shape, and fill the matching solution between the tissues and the imaging cavity to attenuate unnecessary optical signal(s). The second method is to use a camera to scan an outer surface of the tissues to obtain a contour of the tissues as a boundary condition.

However, the first method of using the imaging cavity will increase the complexity of the system, and the matching solution needs to contact with the human body, which will greatly reduce the patient's medical experience and is not suitable for the specific scene of breast detection. The advantage of the second method is to abandon the imaging cavity and the matching solution, and improve the patient's comfort. However, the problem of the second method is that it is easily limited by the space and the camera field of view, and needs to rotate to obtain a whole image of the breast tissues.

SUMMARY OF THE DISCLOSURE

In order to solve the above problems in the related arts, the disclosure provides a breast diffusion optical tomography device, a diffusion optical tomography system and a method for obtaining a breast surface contour. The technical problem to be solved by the disclosure can be addressed by following technical solutions.

A breast diffusion optical tomography device may include a light source, a detector and an acquisitor. The light source and the detector are movable along a preset direction. The light source includes a continuous-wave mode light source and a frequency-domain mode light source. The detector includes a continuous-wave mode detector and a frequency-domain mode detector. The acquisitor includes a continuous-wave mode acquisitor and a frequency-domain mode acquisitor. The continuous-wave mode light source includes M1 number of multi-wavelength light emitters, and the frequency-domain mode light source includes M2 number of laser diodes of different wavelengths. The continuous-wave mode detector includes N1 number of silicon photomultipliers, and the frequency-domain mode detector includes N2 number of silicon photomultipliers. The M1 number of multi-wavelength light emitters, M2 number of laser diodes, N1 number of silicon photomultipliers and N2 number of silicon photomultipliers each are set with an evenly spaced arrangement. The N1 number of silicon photomultipliers are connected to the continuous-wave mode acquisitor, and the N2 number of silicon photomultipliers are connected to the frequency-domain mode acquisitor.

In an embodiment of the disclosure, the breast diffusion optical tomography device further includes a light source switcher. The light source switcher includes multiple first analog switches, a second analog switch, multiple first decoders and a second decoder. First output terminals of the continuous-wave mode acquisitor are correspondingly connected to multiple first input terminals of each of the first analog switches and multiple first input terminals of the second analog switch, multiple second output terminals of the continuous-wave mode acquisitor are correspondingly connected to multiple input terminals of each of the first decoders, and third output terminals of the continuous-wave mode acquisitor are correspondingly connected to multiple input terminals of the second decoder. Each output terminal of the second decoder is connected to an enable terminal of one of the first decoders, one of output terminals of each of the first decoders is connected to an enable terminal of one of the first analog switches, output terminals of each of the first analog switches are correspondingly connected to light emitters of a same wavelength in a same row of the multi-wavelength light emitters, and one output terminal of one of the first decoders is connected to an enable terminal of the second analog switch.

In an embodiment of the disclosure, the breast diffusion optical tomography device further includes a driving module (also referred to as driving circuit). The driving module includes a first capacitor C1, a first resistor R1, a second resistor R2, a transistor Q and multiple third resistors R3. An analog output terminal of the continuous-wave mode acquisitor is connected to a first terminal of the first resistor R1, a first terminal of the second resistor R2 and a base electrode of the transistor Q through the first capacitor C1. A second terminal of the first resistance R1 is connected to a grounding terminal. An emitter electrode of the transistor Q is connected to the grounding terminal, a collector electrode of the transistor Q is connected to second input terminals of the first analog switches and a second input terminal of the second analog switch. The output terminals of each of the first analog switches are connected to cathodes of the light emitters of the same wavelength in the same row of the multi-wavelength light emitters through the third resistors R3. Each output terminal of the second analog switch is connected to a cathode of one of the laser diodes through the third resistor R3. Anodes of all the light emitters and anodes of the laser diode are together connected to the second terminal of the second resistor R2 and a power supply terminal.

In an embodiment of the disclosure, the light source includes plate-shaped structure.

In an embodiment of the disclosure, the detector includes a plate-shaped structure.

In an embodiment of the disclosure, the breast diffusion optical tomography device further includes multiple temperature sensors. The temperature sensors are arranged on the plate-shaped structure, and the temperature sensors are connected to the continuous-wave mode acquisitor.

In an embodiment of the disclosure, the breast diffusion optical tomography device further includes a mechanical motion module (also referred to as mechanical driver). The mechanical motion module includes two sliders, a screw rod, a slide rail and a motor. The light source and the detector are respectively arranged on the two sliders, the screw rod passes through screw holes of the two sliders, and one end of the screw rod is connected to the motor. The screw rod includes a first screw rod part and a second screw rod part, and spiral directions of the first screw rod part and the second screw rod part are opposite to each other. The first screw rod part passes through the screw hole of one of the sliders, the second screw rod part passes through the screw hole of the other of the sliders, and bottom ends of the sliders are arranged on the slide rail.

A diffusion optical tomography system based on square wave modulation is provided in another embodiment of the disclosure. The diffusion optical tomography system includes the breast diffusion optical tomography device described in any of the above embodiments, and the diffusion optical tomography system further includes a square-wave generator and a light source driver. The square-wave generator is configured (i.e., structured and arranged) to obtain a square wave according to a sine wave. The light source driver is connected to the light source driver and configured to apply the square wave to the light emitters of the light source and thereby drive the light emitters to emit light beams for irradiating/illuminating an object to be measured. The detector is configured to detect an optical signal generated by the light beams emitted from the light emitters passing through the object to be measured and convert the optical signal into an electrical signal.

In an embodiment of the disclosure, the square-wave generator includes a microcontroller unit (MCU), a direct digital synthesizer (DDS) module, a comparison module, a direct current (DC) voltage source and an addition module. The MCU is connected to the DDS, the DDS is connected to the comparison module, and the comparison module and the DC voltage source are connected to the addition module.

The DDS is configured to generate the sine wave according to a control of the MCU.

The comparison module is configured to obtain a first square wave according to the sine wave.

The addition module is configured to obtain a second square wave according to a voltage amplitude of the first square wave and a DC voltage provided by the DC voltage source, and a voltage amplitude of the second square wave is a positive voltage.

In an embodiment of the disclosure, the light source driver includes a second capacitor C2, a fourth resistor R4, a fifth resistor R5, a sixth resistor R6, (M1+M2) number of light emitters, a transistor Q1 and a DC power supply.

A first terminal of the second capacitor C2 is connected to the addition module, a second terminal of the second capacitor C2 is connected to a first terminal of the fourth resistor R4 and a base electrode of the transistor Q1, the sixth resistor R6 is connected in series between an emitter electrode of the transistor Q1 and an grounding terminal, a second terminal of the fourth resistor R4 is connected to a first terminal of the fifth resistor R5 and a positive electrode of the DC power supply, anodes of the (M1+M2) number of light emitters are together connected to a second terminal of the fifth resistor R5, cathodes of the (M1+M2) number of light emitters are together connected to a collector electrode of the transistor Q1, and a negative electrode of the DC power supply is connected between the sixth resistor R6 and the grounding terminal.

In an embodiment of the disclosure, the detector includes multiple silicon photomultipliers which are connected in parallel.

In an embodiment of the disclosure, the light emitters include LEDs.

In an embodiment of the disclosure, the diffusion optical tomography system further includes a band-pass filter. The band-pass filter is connected to the detector, and the band-pass filter is used to filter out harmonic waves in the second square wave and retain a fundamental wave in the second square wave to obtain the filtered signal.

In an embodiment of the disclosure, the band-pass filter includes a window function module, a first fast Fourier transform module, a second fast Fourier transform module, a multiplication module and an inverse Fourier transform module. The window function module is connected to the first fast Fourier transform module, and the detector is connected to the second fast Fourier transform module. The first fast Fourier transform module and the second fast Fourier transform module are connected to the multiplication module, and the multiplication module is connected to the inverse Fourier transform module.

The window function module is used for providing a window function.

The first fast Fourier transform module is used for performing a Fourier transform on the window function to obtain a first group of values.

The second fast Fourier transform module is used to perform a Fourier transform on the electrical signal provided by the detector to obtain a second group of values.

The multiplication module is used for multiplying the first group of values with the second group of values to obtain the third group of values.

The inverse Fourier transform module is used for performing an inverse Fourier transform on the third group of values to obtain the filtered signal.

In an embodiment of the disclosure, the diffusion optical tomography system also includes an amplitude module (also referred to as amplitude obtainer). The amplitude module is connected to the band-pass filter. The amplitude module includes a first left shift module, a first accumulation module, a first average value calculation module, a third fast Fourier transform module and a first amplitude calculation module.

The first left shift module is connected to the band-pass filter, and is used to perform a shift processing on the filtered signal according to a preset method to obtain multiple first shift signals.

The first accumulation module is connected to the first left shift module and used for accumulating the filtered signal and the first shift signals to obtain the first accumulation signal.

The first average value calculation module is connected to the first accumulation module and used to obtain a first average signal according to the first accumulation signal and a length of the filtered signal.

The third fast Fourier transform module is connected to the first average value calculation module and is used to perform a Fourier transform on the first average signal to obtain a fourth group of values.

The first amplitude calculation module is connected to the third fast Fourier transform module and used to obtain a first preset value in the fourth group of values and then obtain an amplitude according to a real part and an imaginary part of the first preset value.

In an embodiment of the disclosure, the light emitters include LDs (laser diodes). The detector includes silicon photomultipliers.

In an embodiment of the disclosure, the diffusion optical tomography system also includes an amplitude and phase calculator. The amplitude and phase calculator is connected to the detector, and the amplitude and phase calculator includes a second left shift module, a second accumulation module, a second average value calculation module, a fourth fast Fourier transform module, a second amplitude calculation module and a phase calculation module.

The second left shift module is connected to the detector and used to perform a shift processing on the electrical signals outputted by the detector according to a preset method to obtain multiple second shift signals.

The second accumulation module is connected to the second left shift module and used for accumulating the electrical signal and the second shift signals to obtain the second accumulation signal.

The second average value calculation module is connected to the second accumulation module and used to obtain a second average signal according to the second accumulation signal and a bit number of the electrical signal.

The fourth fast Fourier transform module is connected to the second average value calculation module and used to perform Fourier transform on the second average signal to obtain a fifth group of values.

The second amplitude calculation module is connected to the fourth fast Fourier transform module and used to obtain a second preset value from the fifth group of values and then obtain an amplitude according to a real part and an imaginary part of the second preset value.

The phase calculation module is connected to the fourth fast Fourier transform module and used to obtain the second preset value from the fifth group of values and then obtain a phase value according to the real part and the imaginary part of the second preset value.

A method for obtaining a breast surface contour is further provided in still another embodiment of the disclosure. The method for obtaining a breast surface contour uses the breast diffusion optical tomography device described in any of the above embodiments for imaging, and the method for obtaining a surface contour of the breast includes the following steps of:

acquiring at least three source coordinate points in a first coordinate system, and the at least three source coordinate points being not on a same straight line;

obtaining a first system matrix and a second system matrix according to the at least three source coordinate points;

obtaining a spliced point cloud image according to the first system matrix, a first point cloud image and a third point cloud image;

obtaining a registered point cloud image according to the spliced point cloud image and the second system matrix; and obtain a breast surface contour image according to the registered point cloud image.

In an embodiment of the disclosure, the step of obtaining a first system matrix and a second system matrix according to the at least three source coordinate points, includes:

obtaining a first coordinate point according to a coordinate position of the source coordinate point in a second coordinate system;

rotating the first coordinate point around a preset axis of the second coordinate system to a third coordinate system to thereby obtain the first system matrix;

obtaining a second coordinate point according to a coordinate position of the source coordinate point in the third coordinate system; and rotating the second coordinate point around a preset axis of the third coordinate system to the first coordinate system to thereby obtain the second system matrix.

In an embodiment of the disclosure, the step of obtaining a spliced point cloud image according to the first system matrix, a first point cloud image and a third point cloud image, includes:

acquiring coordinate values of first points in the first point cloud image;

obtaining a second point cloud image according to the coordinate values of the first points and the first system matrix; and obtaining the spliced point cloud image according to the third point cloud image and the second point cloud image.

In an embodiment of the disclosure, the step of obtaining a registered point cloud image according to the spliced point cloud image and the second system matrix includes:

acquiring coordinate values of second points in the spliced point cloud image; and obtaining the registered point cloud image according to the coordinate values of the second points and the second system matrix.

In an embodiment of the disclosure, the step of obtaining a breast surface contour image according to the registered point cloud image includes:

performing a surface fitting processing on the registered point cloud image to obtain a fitting image;

obtaining a closed contour point cloud image by performing a point sampling and a point cloud complement processing on the fitting image; and obtaining the breast surface contour image according to the closed contour point cloud image.

In an embodiment of the disclosure, the step of performing a surface fitting processing on the registered point cloud image to obtain a fitting image includes:

using a least square method to perform the surface fitting processing on the registered point cloud image to obtain the fitting image.

In an embodiment of the disclosure, the step of obtaining the breast surface contour image according to the closed contour point cloud image includes:

using a triangular finite element method to perform a surface contour mesh construction on the closed contour point cloud image to obtain a surface contour image; and performing a mesh generation processing on the surface contour image to obtain the breast surface contour image.

Embodiments of the disclosure mainly can achieve beneficial effects as follows.

The breast diffusion optical tomography device provided by the disclosure uses surface-mounted devices to directly contact the patient's breast tissues, which can avoid the use of optical fiber and reduces the system complexity. Moreover, the silicon photomultipliers are used to replace PMT or CCD, the system cost can be reduced. In addition, the breast diffusion optical tomography device associated with the disclosure can obtain the breast contour by using the contour fast scanning scheme, which can reduce the system complexity and improve the comfort of patients.

The disclosure will be further described in detail below in conjunction with accompanying drawings and embodiments.

DETAILED DESCRIPTION OF EMBODIMENTS

The disclosure will be further described in detail in combination with specific embodiments, but embodiments of the disclosure are not limited to these.

First Embodiment

Figure 2:
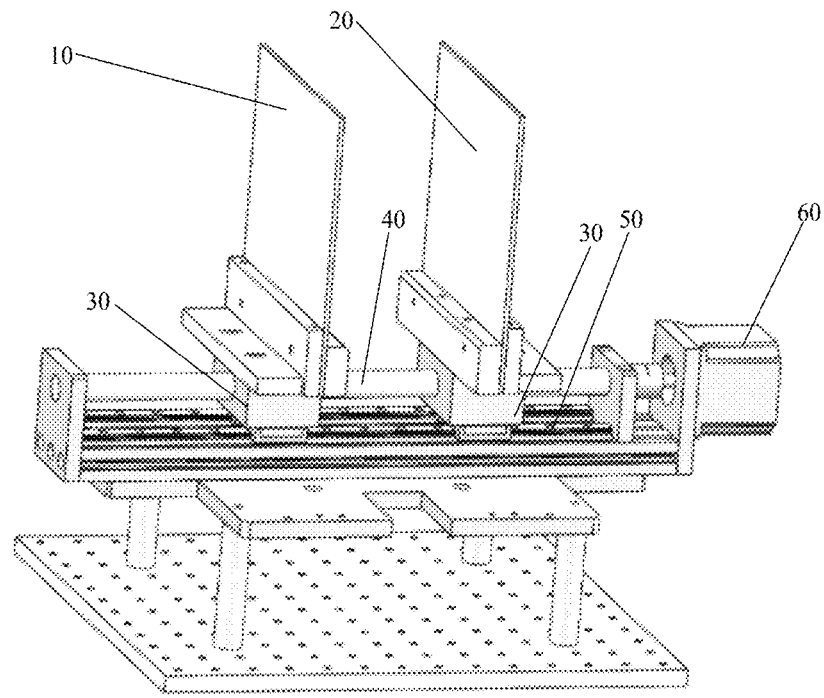
FIG. 2 is a schematic structural view of a breast diffusion optical tomography device according to an embodiment of the disclosure.

FIG. 2 is a schematic structural view of a breast diffusion optical tomography device provided by an embodiment of the disclosure. The breast diffusion optical tomography device includes a light source 10, a detector 20 and an acquisition device (also referred to as acquisitor); and the light source 10 and the detector 20 both are movable along a preset direction. The light source includes a continuous-wave mode light source and a frequency-domain mode light source. The detector includes a continuous-wave mode detector and a frequency-domain mode detector. The acquisitor includes a continuous-wave mode acquisitor and a frequency-domain mode acquisitor. The continuous-wave mode light source includes M1 number of multi-wavelength light emitters for a continuous-wave mode, and the frequency-domain mode light source includes M2 number of laser diodes with different wavelengths for a frequency-domain mode. The continuous-wave mode detector includes N1 number of silicon photomultipliers (SiPMs) for a detection in the continuous-wave mode, and the frequency-domain mode detector includes N2 number of silicon photomultipliers for a detection in the frequency-domain mode. An arrangement of the M1 number of multi-wavelength light emitters, an arrangement of the M2 number of laser diodes, an arrangement of the N1 number of silicon photomultipliers and an arrangement of the N2 number of silicon photomultipliers each are a uniform spacing arrangement (i.e., evenly spaced arrangement). The N1 number of silicon photomultipliers are connected to the continuous-wave mode acquisitor, and N2 number of silicon photomultipliers are connected to the frequency-domain mode acquisitor.

Specifically, the M1 number of multi-wavelength light emitters may for example be arranged in an array, arranged in decreasing row by row, or arranged in other manner, and the embodiment of the disclosure is not specifically limited. The M1 number of multi-wavelength light emitters and the M2 number of laser diodes are integrated onto a plate-shaped structure. Moreover, some of the silicon photomultipliers for the detection in the continuous-wave mode may also be integrated onto the plate-shaped structure integrated with the light sources, the rest of the silicon photomultipliers for the detection in the continuous-wave mode and all the silicon photomultipliers for the detection in the frequency-domain mode can be integrated onto another plate-shaped structure opposite to the plate-shaped structure integrated with light sources. In addition, in an alternative embodiment, all the silicon photomultipliers may be integrated onto a plate-shaped structure opposite to the light sources.

For example, when the M1 number of multi-wavelength light emitters are arranged in an array, the light source 10 includes m1 row and n1 column of multi-wavelength light emitters, and m2 row and n2 column of laser diodes with different wavelengths. Each of the multi-wavelength light emitter includes N number of light emitters with different wavelengths. The detector 20 includes m1 row and n1 column of silicon photomultipliers. The m1 row and n1 column of light emitters are arranged opposite to the m1 row and n1 column of silicon photomultipliers. Adjacent two rows of light emitters have one row of the laser diodes arranged therebetween. The m1 row and n1 column of silicon photomultipliers are connected to the continuous-wave mode acquisitor, and the silicon photomultipliers arranged between two rows of the laser diodes are also connected to the frequency-domain mode acquisitor. The m1 row and n1 column of silicon photomultipliers are all arranged in the array formed by the m1 row and n1 column of multi-wavelength light emitters, and wavelengths of the silicon photomultipliers are different from one another. Each of the multi-wavelength light emitters is for example a multi-wavelength LED or a multi-wavelength LD (laser diode).

In the illustrated embodiment, the light source 10 integrated with the multi-wavelength light emitters and the laser diodes is arranged opposite to the detector 20 integrated with the silicon photomultipliers. The light source 10 is used to provide a light (also referred to as excitation light), and the detector 20 is used to detect the light transmitted through a breast. Since both the light source 10 and the detector 20 are movable along the predetermined direction, the breast can be squeezed and relaxed. The predetermined direction is a moving direction of the light source 10 and the detector 20, for example, a horizontal direction. The light source 10 of the illustrated embodiment includes m1 row and n1 column of multi-wavelength light emitters used in a continuous-wave mode, and each of the multi-wavelength light emitters can be composed of N number of light emitters with different wavelengths. The light source 10 further includes m2 row and n2 column of laser diodes used in a frequency-domain mode, where m2 is less than m1, and n2 is less than n1. A spacing between adjacent two rows of the multi-wavelength light emitters is equal to a spacing between adjacent two rows of the laser diodes, and one row of the laser diodes should be arranged between adjacent two rows of the multi-wavelength light emitters. In addition, the detector 20 includes m1 row and n1 column of silicon photomultipliers, the silicon photomultipliers of the detector 20 and the multi-wavelength light emitters of the light source 10 are arranged in a one-to-one correspondence manner to facilitate the detection, and each of the silicon photomultipliers is connected to the continuous-wave mode acquisitor. The continuous-wave mode acquisitor is used to collect data obtained by the multi-wavelength light emitters irradiating the breast and detected by the detector 20. The continuous-wave mode acquisitor (also referred to as continuous-wave mode acquisition unit) is a low-frequency data acquisition card with sampling frequency of 4 kHz for a single channel. In addition, the one row of silicon photomultipliers between adjacent two rows of laser diodes are also connected to the frequency-domain mode acquisitor (also referred to as frequency-domain mode acquisition unit). The frequency-domain mode acquisitor is used to collect the data obtained by the laser diodes irradiating the breast and detected by the detector 20, which is a high-frequency data acquisition card with sampling frequency of 100 MHz for a single channel.

Figure 3:
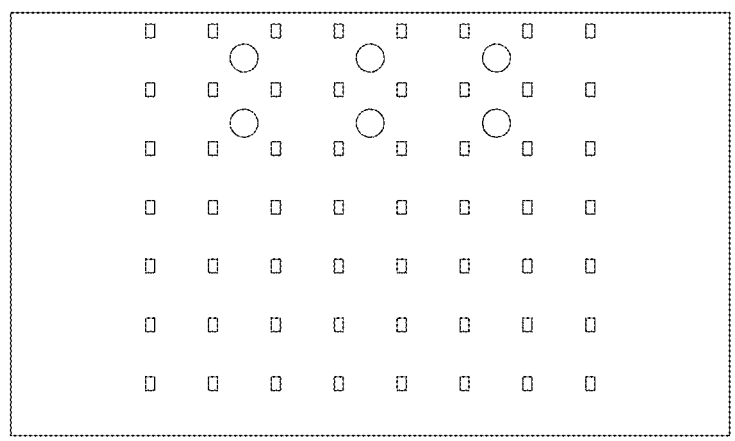
FIG. 3 is a schematic view of a light source according to an embodiment of the disclosure.

For example, referring to FIG. 3, the multi-wavelength light emitter is a three-wavelength light emitter composed of three light-emitting diodes with wavelengths at 660 nm, 750 nm and 840 nm respectively. The light source 10 is equipped with 56 number of multi-wavelength light-emitting diodes arranged in a 7×8 array with a row spacing of 13 mm and a column spacing of 14 mm. The light source 10 is further equipped with 6 laser diodes arranged in a 2×3 array with a row spacing of 13 mm and a column spacing of 28 mm. The wavelengths of the six laser diodes are 905 nm, 850 nm, 830 nm, 808 nm, 780 nm and 685 nm respectively. The first row of the laser diodes is arranged between the first and the second row of the multi-wavelength light-emitting diodes, and the second row of the laser diodes is arranged between the second and the third row of the multi-wavelength light-emitting diodes.

In an illustrated embodiment, the breast diffusion optical tomography device further includes a light source switching module (also referred to as light source switcher). The light source switcher includes a plurality of first analog switches, a second analog switch, a plurality of first decoders, and a second decoder. The number of the first analog switches is T1, and the number of the first decoders is T2. A plurality of first output terminals of the continuous-wave mode acquisitor are correspondingly connected to a plurality of first input terminals of each of the first analog switches and a plurality of first input terminals of the second analog switch. A plurality of second output terminals of the continuous-wave mode acquisitor are correspondingly connected to a plurality of input terminals of each of the first decoders. A plurality of third output terminals of the continuous-wave mode acquisitor are correspondingly connected to a plurality of input terminals of the second decoder. Each output terminal of the second decoder is connected to an enable terminal of one of the first decoders, an output terminal of each of the first decoders is connected with an enable terminal of one of the first analog switches. A plurality of output terminals of each of the first analog switches are correspondingly connected to the light-emitting diodes with a same wavelength in the same row of the multi-wavelength light-emitting diodes, and one output terminal of one of the first decoders is connected to an enable terminal of the second analog switch.

For example, when the M1 number of multi-wavelength light emitters are arranged in an array, each of the first analog switches controls the light emitters with a same wavelength in a same row. Because each of the multi-wavelength light emitters includes N number of light emitters of different wavelengths, and the light source 10 is provided with m1 rows in total, the number of the first analog switches is N×m1. Since the light emitters of the same wavelength can be controlled by one first decoder, one of the output terminals of each first decoder can be connected to the enable terminal of one first analog switch, and all the first analog switches that control on and off of the light emitters of the same wavelength are connected to the same one of the first decoders. In addition, the second analog switch controls all the laser diodes, and its enable terminal is connected to the output terminal of one of the first decoders. The first output terminals of the continuous-wave mode acquisitor are correspondingly connected to the first input terminals of each first analog switch and the first input terminals of the second analog switch, which are used to switch on the light emitters correspondingly controlled by the first analog switches when the first analog switches are enabled, or turn on the laser diodes correspondingly controlled by the second analog switch when the second analog switch is enabled. The second output terminals of the continuous-wave mode acquisitor are correspondingly connected to the input terminals of each of the first decoders, so that the continuous-wave mode acquisitor can correspondingly control the first analog switches or the second analog switch to be enabled through the first decoders. In the illustrated embodiment, the first decoders are enabled by one second decoder, and therefore the third output terminals of the continuous-wave mode acquisitor are connected with the input terminals of the second decoder correspondingly, and one of output terminals of the second decoder is connected with one enable terminal of one of the first decoders correspondingly. In this way, the multi-wavelength light emitters and the laser diodes of the light source 10 can be turned on and off as per actual needs.

Figure 4:
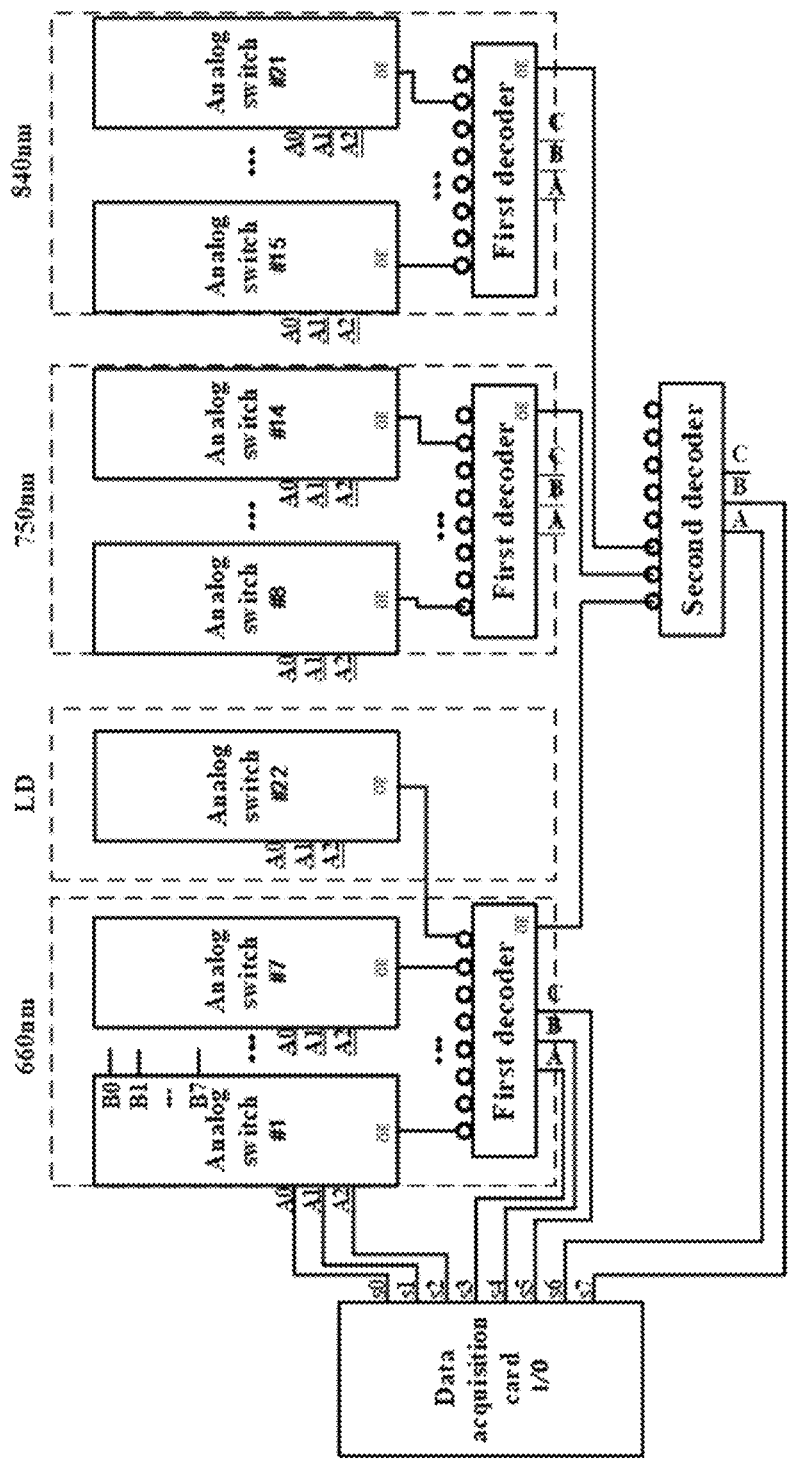
FIG. 4 is a schematic view of a light source switching module according to an embodiment of the disclosure.

For example, referring to FIG. 4, according to the light source 10 provided in FIG. 3, FIG. 4 uses 21 number of first analog switches in total, i.e., analog switch #1 through analog switch #21. The analog switch #1 through the analog switch #7 respectively control the light-emitting diodes with a wavelength of 660 nm in the first row through the seventh row, the analog switch #8 through the analog switch #14 respectively control the light-emitting diodes with a wavelength of 750 nm in the first row through the seventh row, and the analog switch #15 through the analog switch #21 respectively control the light-emitting diodes with a wavelength of 840 nm in the first row through the seventh row. Moreover, a second analog switch is further used, i.e., analog switch #22. The continuous-wave mode acquisitor is a data acquisition card. A first output terminal S0, a first output terminal S1 and a first output terminal S2 of the data acquisition card are respectively connected to a first input terminal A0, a first input terminal A1 and a first input terminal A2 of each of the analog switch #1 through the analog switch #21 and a first input terminal A0, a first input terminal A1 and a first input terminal A2 of the analog switch #22. A second output terminal S3, a second output terminal S4 and a second output terminal S5 of the data acquisition card are respectively connected to an input terminal A, an input terminal B and an input terminal C of each of the first decoders. Seven output terminals of the first one of the first decoders are respectively connected to/with the enable terminals of the analog switch #1 through the analog switch #7, and the other output terminal of the first one of the first decoders is connected with an enable terminal of the analog switch #22. Seven output terminals of the second one of the first decoders are respectively connected with the enable terminals of the analog switch #8 through the analog switch #14, and seven output terminals of the third one of the first decoders are respectively connected with the enable terminals of the analog switch #15 through the analog switch #21. In addition, the third output terminals S6 and S7 of the data acquisition card are respectively connected with the input terminals A and B of the second decoder, and three output terminals of the second decoder are respectively connected with the enable terminals of the three first decoders. For example, when the analog switch #1 is enabled, if the first input terminal A0, the first input terminal A1 and the first input terminal A2 of the analog switch #1 are 000, the first light-emitting diode controlled by the analog switch #1 is turned on; if they are 001, the second light-emitting diode controlled by the analog switch #1 is turned on, and so on. The first and the second decoders each is a 3-8 decoder. The light source integrated on the plate-shaped structure has (56×3+6) number of light sources. The light-emitting diodes are divided into three groups according to their wavelengths, and each group uses seven 8-way analog switches to correspond with 56 multi-wavelength light-emitting diodes in one-by-one manner. The I/O signals S0-S2 of the data acquisition card are connected to input/selection pins of all the analog switches in parallel to output input currents to turned-on/selected light-emitting diodes. Each group is further equipped with a 3-8 decoder, and output terminals of the 3-8 decoder is connected with the enable terminals of the seven analog switches. The I/O signals S3-S5 of the data acquisition card are connected to the input terminals of the 3-8 decoders in parallel to realize the enabling of the analog switches. Finally, another 3-8 decoder is designed to enable the 3-8 decoders in different wavelength groups and controlled by the I/O signals S6 and S7 of the data acquisition card.

Figure 5:
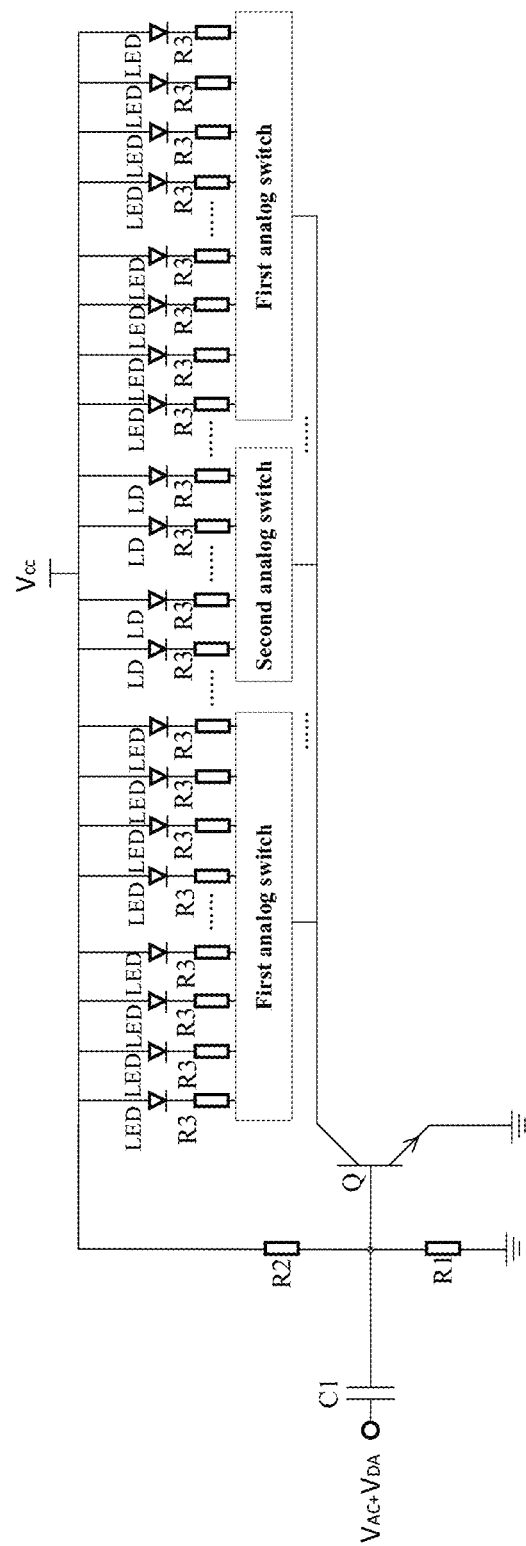
FIG. 5 is a schematic view of a driving module according to an embodiment of the disclosure.

In an illustrated embodiment, referring to FIG. 5, the breast diffusion optical tomography (DOT) device further includes a driving module (also referred to as driving circuit). The driving circuit includes a first capacitor C1, a first resistor R1, a second resistor R2, a transistor Q and a plurality of (i.e., more than one) third resistors R3. An analog output terminal of the continuous-wave mode acquisitor is connected with a first terminal of the first resistor R1, a first terminal of the second resistor R2 and a base electrode of the transistor Q through the first capacitor C1. A second terminal of the first resistance R1 is connected to a grounding terminal (i.e., grounded). An emitter electrode of the transistor Q is connected to the grounding terminal, and a collector electrode of the transistor Q is connected with second input terminals of the first analog switches and a second input terminal of the second analog switch. Output terminals of the first analog switch are connected to cathodes of the light emitters of a same wavelength in a same row of the multi-wavelength light emitters through the third resistors R3. Output terminals of the second analog switch are connected to cathodes of the laser diodes through the third resistors R3, and anodes of all the light emitters and anodes of the laser diodes are together connected to a second terminal of the second resistance R2 and a power supply terminal.

In the illustrated embodiment, the driving circuit is disposed with the transistor Q, a current on the collector electrode of the transistor Q is used to drive the light emitters and the laser diodes, and the analog output (DA) terminal of the continuous-wave mode acquisitor is connected to the base electrode of the transistor Q, so that a static working point of the transistor Q can be changed by changing a magnitude on the analog output terminal of the continuous-wave mode acquisitor, and driving currents for the light emitters and the laser diodes can be controlled consequently.

Preferably, the light source 10 includes a plate-shaped structure, and the detector 20 also includes a plate-shaped structure, that is, all multi-wavelength light emitters and all laser diodes are arranged on a plate-shaped structure, and all silicon photomultipliers are also arranged on a plate-shaped structure, so as to facilitate a clamping of a breast. In addition, for the safety and comfort of patients, a black silicone cushion with a thickness of 2 mm can be placed on the plate-shaped structure with the multi-wavelength light emitters and the laser diodes, and the black silicone cushion needs to be provided with multiple (i.e., more than one) through holes to expose the multi-wavelength light emitters and the laser diodes.

In an illustrated embodiment, the fiber-free flat breast diffusion optical tomography device can further include a plurality of temperature sensors. The temperature sensors are used to monitor temperatures of parts of the detector 20 in contact with tissues of the breast in real time, and thereby to avoid a damage to the breast resulting from an excessively high temperature of the detector 20. The temperature sensors are arranged on the plate-shaped structure. The temperature sensors are connected with the continuous-wave mode acquisitor to obtain the temperatures of the parts of the detector 20 in contact with the tissues of the breast in time. For example, the number of the temperature sensors is 4. There is no limit on specific positions of the temperature sensors in the illustrated embodiment, as long as the temperatures of the parts of the detector 20 in contact with the tissues of the breast can be measured during detection.

Figure 1:
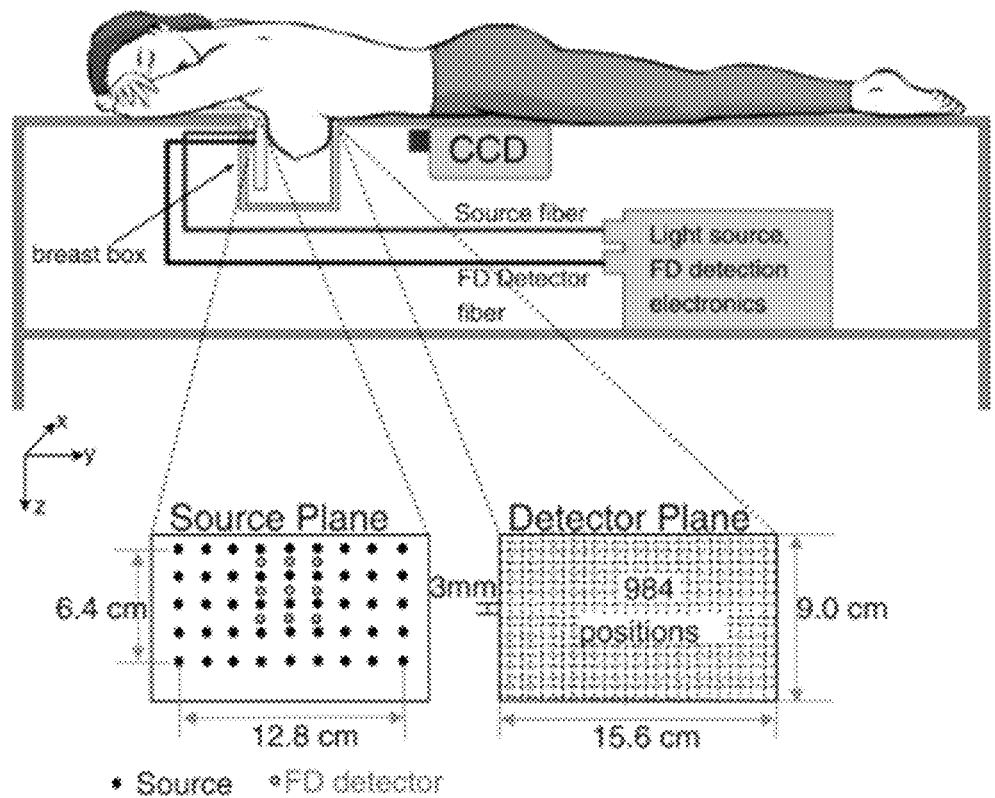
FIG. 1 is a schematic diagram of a breast imaging method according to the related art.
Figure 6:
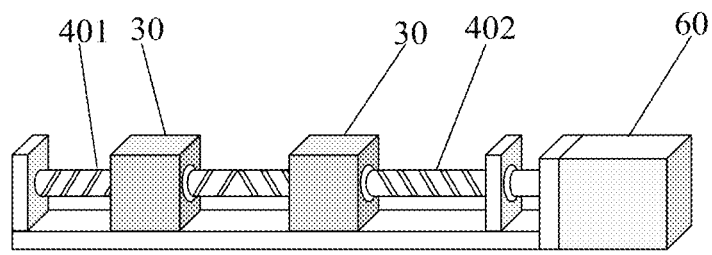
FIG. 6 is a schematic view of a mechanical motion module according to an embodiment of the disclosure.

In an illustrated embodiment, referring to FIG. 1 and FIG. 6, the breast diffusion optical tomography device further includes a mechanical motion module (also referred to as mechanical driver). The mechanical motion module includes two sliders 30, a screw rod 40, a slide rail 50 and a motor 60. The light source 10 and the detector 20 are arranged on the two sliders 30, respectively. The screw rod 40 passes through screw holes of the two sliders 30, and one end of the screw rod 40 is connected with the motor 60. The screw rod 40 includes a first screw rod part 401 and a second screw rod part 402, and spiral directions of the first screw rod part 401 and the second screw rod part 402 are mutually opposite to each other. The first screw rod part 401 passes through the screw hole of one of the sliders 30, the second screw rod part 402 passes through the screw hole of the other of the sliders 30, and bottom ends of the sliders 30 are arranged on the slide rail 50.

In other words, in the illustrated embodiment, one of the sliders 30 is fixedly installed with the light source 10, and the other of the sliders 30 is fixedly installed with the detector 20. The sliders 30 each are provided with a screw hole. Because the screw rod 40 includes a first screw rod part 401 and a second screw rod part 402 with mutually opposite spiral/thread directions, the first screw rod part 401 passes through the screw hole of one of the sliders 30, and the second screw rod part 402 passes through the screw hole of the other of the sliders 30. Therefore, when the screw rod 40 is rotated, the two sliders 30 will move in opposite directions respectively, so that the light source 10 and the detector 20 respectively arranged on the two sliders 30 can move in opposite directions, and thereby a spacing between the light source 10 and the detector 20 can be adjusted. The slide rail 50 is correspondingly arranged under the sliders 30, and the sliders 30 can move along the slide rail 50.

Preferably, the motor 60 is a stepper motor with an encoder.

In the illustrated embodiment, in order to squeeze and relax breast tissues, the light source 10 and the detector 20 are respectively placed on two movable sliders coaxial with each other. The mechanical motion module uses the stepper motor with encoder. Compared with an open-loop stepper motor without encoder, the encoder enables the stepper motor to accurately record the number of pulses per movement, and thereby avoiding a problem of motor motion losing step. Moreover, after each being powered on, the mechanical motion module can record initial positions of the sliders, so that the sliders can be automatically driven to return to their initial positions after each the system finishes scanning, and there is no need to record the positions manually.

Preferably, a movable stopper can be arranged between the first screw rod part 401 and the second screw rod part 402. The movable stopper is used to limit positions of the two sliders 30. When in use, the movable stopper can be placed at the joint point of the first screw rod part 401 and the second screw rod part 402, and to thereby prevent the two sliders 30 from moving into the opposite screw rod part. In addition, another movable stopper can be installed between the motor and the slider 30 more close to the motor, and to thereby limit a position of the slider 30 more close to the motor. The setting of the two movable stoppers can be used to limit the positions of the two sliders so as not to exceed the movable range, thereby avoiding malfunctions.

Figure 7A:
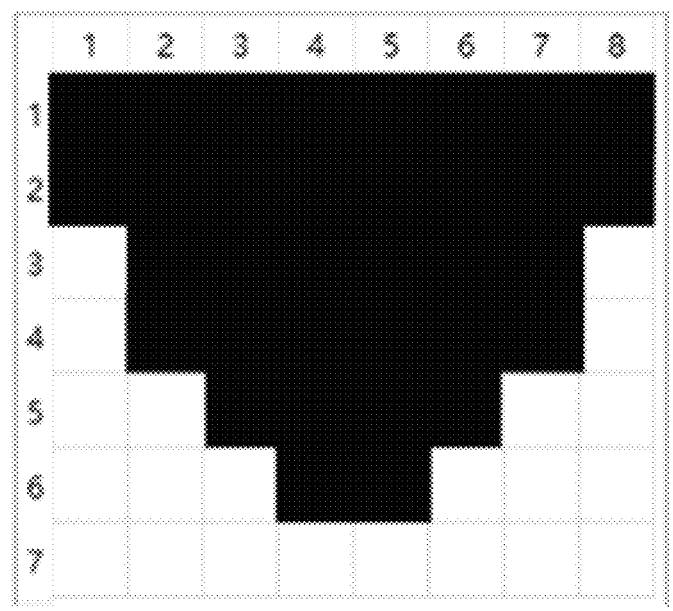
FIGS. 7a-7b are schematic views of fast-scanning results according to an embodiment of the disclosure.
Figure 7B:
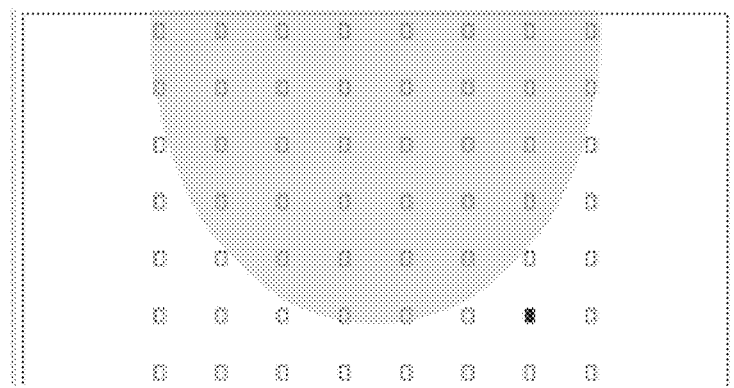

The illustrated breast diffusion optical tomography device can quickly scan the boundary of the breast. When the two plate-shaped structures are placed in parallel and aligned with each other, because relative positions of the multi-wavelength light emitters and the silicon photomultipliers are the same, all the multi-wavelength light emitters and all the silicon photomultipliers are aligned in one-by-one manner. Before a formal data acquisition, the light emitters can be quickly lighted on by traversing, and meanwhile only a signal of the silicon photomultiplier corresponding to each lighted-on light emitter is collected, if the signal is lower than a preset value, it is considered as the light emitter and the corresponding silicon photomultiplier are covered by the breast tissues, whereas if the signal is higher than the preset value, it is considered that the light emitter and the corresponding silicon photomultiplier are not in contact with the breast tissues. The preset value can be set according to an actual situation, which is not specifically limited in the illustrated embodiment. First, the light emitters can be traversed according to sizes/magnitudes of the wavelengths, for example, the light emitters of the same wavelength are traversed by sequentially lighting on as per an order from the first light emitter in the first row to the last light emitter in the last row, and the light emitters are traversed according to a wavelength order from small to large, that is, after all the light emitters of a same wavelength are traversed, then all the light emitters of next same wavelength are traversed. When all the light emitters are traversed, a contour of the contact surface between the breast and the two plate-shaped structures can be obtained. At the same time, a distance between the two plate-shaped structures is known, and therefore a semicylindrical result similar to the breast tissues can be obtained. Referring to FIG. 7a and FIG. 7b, FIG. 7a represents an acquisition result (i.e., the semicylindrical result). If the light emitter at a position and the corresponding silicon photomultiplier touches the breast tissues, the corresponding cell will display as black, otherwise it will display as white. The ellipse in FIG. 7b represents squeezed breast tissues, and each rectangular box represents one light emitter. Through the fast-scanning solution, the contour of breast tissues after being slightly squeezed can be estimated in a short time, and meanwhile whether the breast tissues are located in an appropriate imaging area can also be judged/determined.

Figure 8:
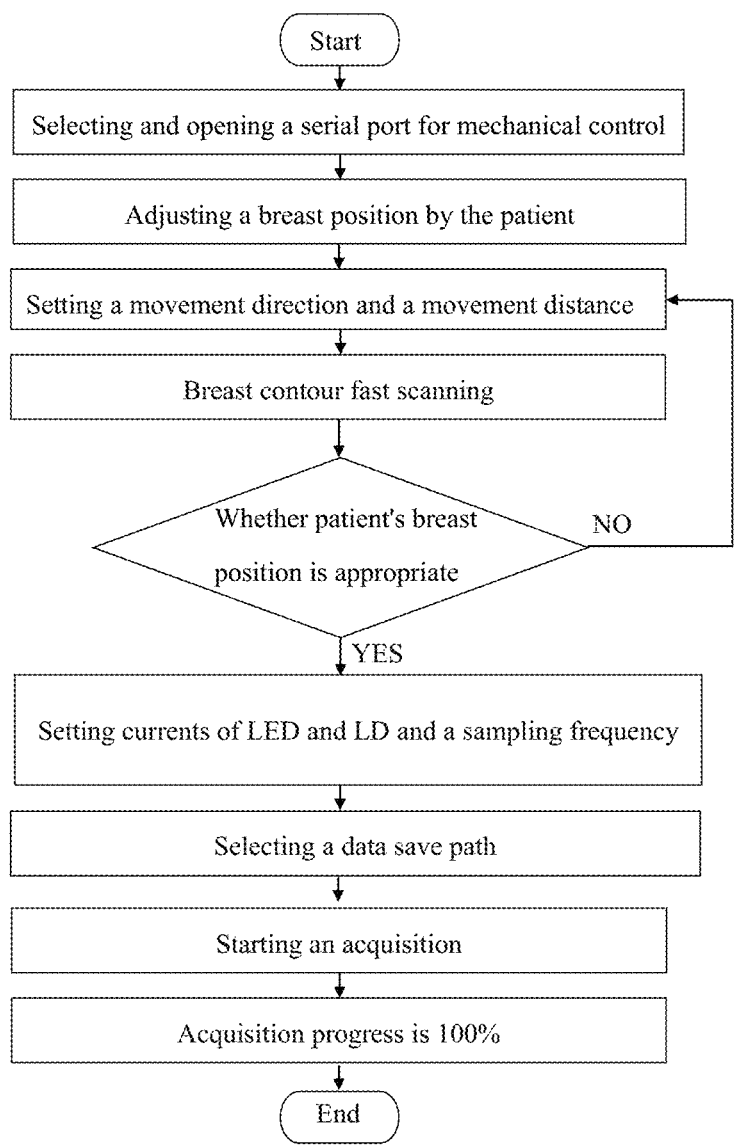
FIG. 8 is a schematic view of an acquisition flow according to an embodiment of the disclosure.
Figure 9:
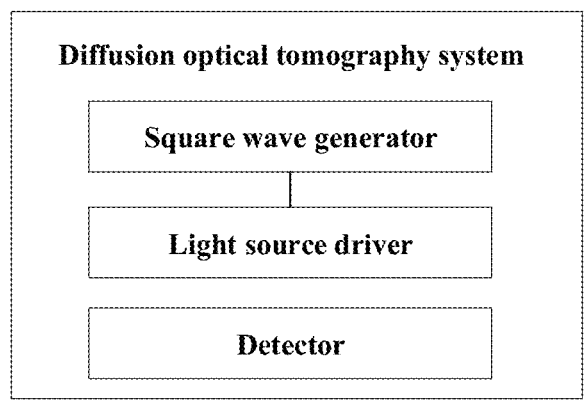
FIG. 9 is a schematic view of a diffusion optical tomography system according to an embodiment of the disclosure.

Referring to FIG. 8, in an actual use, first a serial port for communication with a controller of the mechanical movement module is opened. At the same time, the patient places the breast tissues between the two plate-shaped structures, and the plate-shaped structures will be moved according to preset movement directions and distances. At this time, the operator and the patient will interact with each other in real time to confirm the comfort of the breast tissues. After the plate-shaped structures clamped the breast tissues, the breast contour was scanned quickly. If the breast tissues deviate from a center position of field of vision of the plate-shaped structures, the two plate-shaped structures then are moved away from the breast, and the patient adjusts the position of the breast again. Whereas, when the breast tissues are in the center position, acquisition parameters are started to be set and then the acquisition starts. In a process of data acquisition, the laser diodes with different wavelengths are lighted on firstly, and at the same time signals of the silicon photomultipliers used for a high frequency data acquisition are acquired/collected. Afterwards, the light emitters of different wavelengths in each of the multi-wavelength light emitters are traversed, the data acquisition card acquires/collects the output of all the silicon photomultipliers, and the data acquired/collected by the data acquisition card can be saved in a hard disk in a form of binary stream. After the data acquisition of the data acquisition card is finished, the plate-shaped structures can return to their original positions for next use.

The illustrated breast diffusion optical tomography device provided by the disclosure uses surface mounted devices to directly contact the breast tissues of patients, avoids the use of optical fiber, and reduces the system complexity. Moreover, the silicon photomultipliers are used to replace PMT or CCD, thereby reducing the system cost. The breast diffusion optical tomography device in the illustrated embodiment can obtain the breast contour by using the contour fast-scanning solution, which reduces the system complexity and improves the comfort of patients. In addition, the diffusion optical tomography device of the illustrated embodiment can work in both a steady-state mode (i.e., a continuous-wave mode) and a frequency-domain mode.

Second Embodiment

Based on the first embodiment, a diffusion optical tomography system (also referred to as a non-fiber flat-panel breast diffusion optical tomography system) of the embodiment includes the breast diffusion optical tomography device according to the first embodiment, and the diffusion optical tomography system further includes a square-wave generator and a light source driver. The square-wave generator is used to obtain a square wave according to a sine wave. The light source driver is connected to the square-wave generator, which is used to add the square wave to the light emitters and thereby drive the light emitters to emit light beam, and the light beams emitted by the light emitters illuminate an object to be measured. The detector obtains an electrical signal converted from the light passing through the object to be measured.

That is, the square-wave generator of the illustrated embodiment can obtain the square wave according to a sine wave and then add the square wave to the light emitters through the light source driver, so as to realize a modulation of the light beams emitted from the light emitters, thereby realizing the detection in a frequency-domain mode. The square wave is convenient to generate with a higher modulation depth, and can ensure the stability of the signal as the modulation signal. When the light beams added with square wave illuminate the object to be measured (e.g., breast), the detector will detect the light beams passing through the object to be measured, and the detector can convert a detected light signal into the electrical signal.

Figure 10:
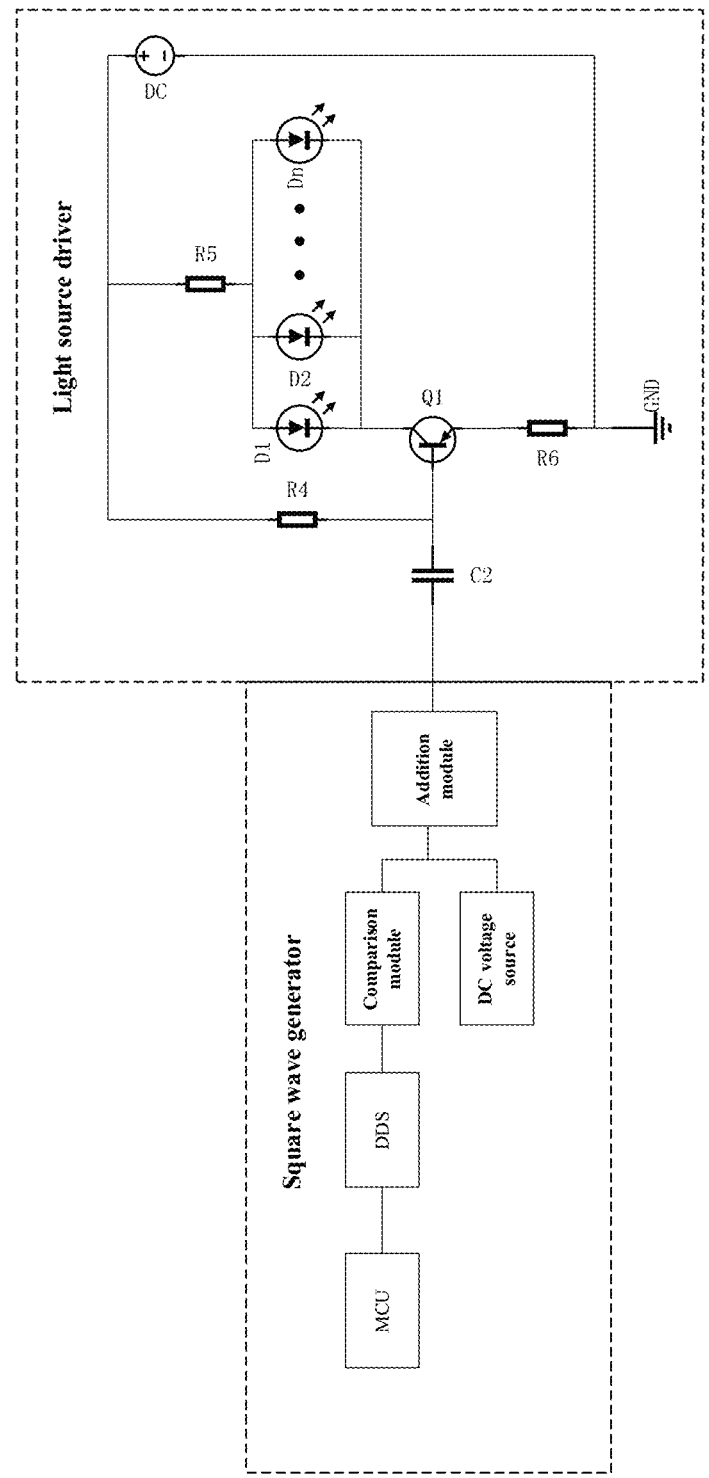
FIG. 10 is a schematic view of a square-wave generator and a light source driver according to an embodiment of the disclosure.

Referring to FIG. 10, in an illustrated embodiment, the square-wave generator includes a MCU (microcontroller unit), a DDS (direct digital synthesizer), a comparison module, a DC (direct current) voltage source and an addition module. The MCU is connected to the DDS, the DDS is connected to the comparison module, and the comparison module and the DC voltage source are connected with the addition module. The DDS is used to generate the sine wave according to a control of the MCU. The comparison module is used to obtain a first square wave according to the sine wave. The addition module is used to obtain a second square wave according to a voltage amplitude of the first square wave and a DC voltage provided by the DC voltage source, and the voltage amplitude of the second square wave is positive voltage.

In other words, under the control of the MCU, the DDS can generate the sine wave, the comparison module will compare the voltage of the sine wave with a threshold of the comparison module, if the voltage of the sine wave is greater than the threshold, the output signal is 1, and if the voltage is less than the threshold, the output signal is 0. The comparison module will convert the sine wave into the first square wave. The comparison module is for example a comparator, and the model of comparator may be LTC6752. Because the square wave as required has no negative voltage, in the illustrated embodiment, the DC voltage provided by the DC voltage source and the voltage amplitude corresponding to the obtained first square wave are added by the addition module. After the addition, the second square wave can be obtained, and the voltage amplitude of the second square wave needs to be a positive voltage. For example, if the voltage amplitude of the first square wave is −1V~+1V, the DC voltage of +2V can be provided by the DC voltage source, and the second square wave with a voltage amplitude of +1V~+3V can be obtained by the adding. The addition module is, for example, an adder.

Referring to FIG. 10, in an illustrated embodiment, the light source driver includes a second capacitor C2, a fourth resistor R4, a fifth resistor R5, a sixth resistor R6, n number of light emitters, a transistor Q1 and a DC power supply. A first terminal of the second capacitor C2 is connected with/to the addition/adding module, a second terminal of the second capacitor C2 is connected with a first terminal of the fourth resistor R4 and a base electrode of the transistor Q1. The sixth resistor R6 is connected in series between an emitter electrode of the transistor Q1 and a grounding terminal. A second terminal of the fourth resistor R4 is connected with a first terminal of the fifth resistor R5 and a positive electrode of the DC power supply. Anodes of the n number of light emitters are together connected to a second terminal of the fifth resistor R5, cathodes of the n number of light emitters are together connected to a collector electrode of the transistor Q1, and a negative electrode of the DC power supply is connected between the sixth resistor R6 and the grounding terminal.

The illustrated embodiment uses the light source driver to apply the second square wave of the square-wave generator onto the light beams emitted by the light emitters, and realizes the modulation of the light beams by using the square wave, thereby obtaining a modulated signal in a frequency-domain mode. The light source driver can realize the driving of the light emitters and thereby drives light emitters to emit light beams to irradiate the object to be measured. The illustrated embodiment has no specific requirement for the arrangement of light emitters, as long as light beams emitted from the light emitters can irradiate/illuminate the object to be measured and can be detected by the detector.

The light emitters of the illustrated embodiment can for example be LEDs (light-emitting diodes) or LDs (laser diodes). The diffusion optical tomography system of the illustrated embodiment can be simultaneously equipped with both the LEDs and the LDs instead, and those skilled in the art can set according to actual needs.

The detector of the illustrated embodiment may include a plurality of silicon photomultipliers (SiPMs), and all of the silicon photomultipliers are connected in parallel. The silicon photomultipliers can detect optical signals passing through the object to be measured and convert the detected optical signals into electrical signals.

The periodic square wave of the diffusion optical tomography system in the illustrated embodiment is formed by a superposition of sine wave signals of multiple frequencies, and various harmonic frequencies increase in order of integer times of a fundamental/base signal frequency. From a perspective of a signal energy distribution, the energy of periodic signal is mainly distributed in a finite harmonic component with low frequency. In the continuous-wave mode, by setting a band-pass filter, filtering the harmonic signals and retaining the fundamental signal, it can be used for reconstructing an image. In the frequency-domain mode, owing to the use of silicon photomultipliers (SiPMs), each of which has a charging time of 23 ns. Due to characteristics limitations of the silicon photomultipliers, they cannot be used to detect a signal with frequency over 43 MHz. Therefore, the square wave modulated signal with a frequency range of 25 MHz~40 MHz can be adopted, the silicon photomultiplier can be a good low-pass filter in the frequency range and thus there is no need of subsequent filter circuit, the fundamental signal can be retained and harmonic components can be filtered.

The diffusion optical tomography system provided by the illustrated embodiment of the disclosure has a simple structure and is easy to be integrated. The diffusion optical tomography system of the illustrated embodiment of the disclosure can ensure the stability of signal by using the square wave to modulate the light emitters.

Third Embodiment

On the basis of the second embodiment, this embodiment specifically describes the diffusion optical tomography system using LEDs as light emitters.

Figure 11:
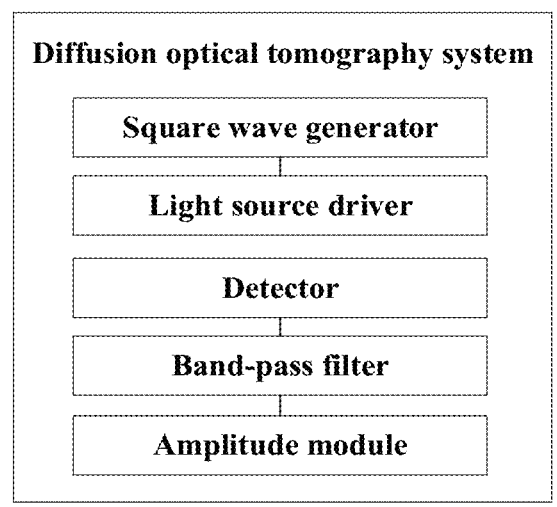
FIG. 11 is a schematic view of another diffusion optical tomography system according to an embodiment of the disclosure.

FIG. 11 is a schematic view of another diffusion optical tomography system provided by an embodiment of the disclosure. When the light emitters are LEDs, the diffusion optical tomography system may further include a band-pass filter. The band-pass filter is connected with the detector used to filter out the harmonic waves in the second square wave and retain the fundamental wave in the second square wave.

Figure 12:
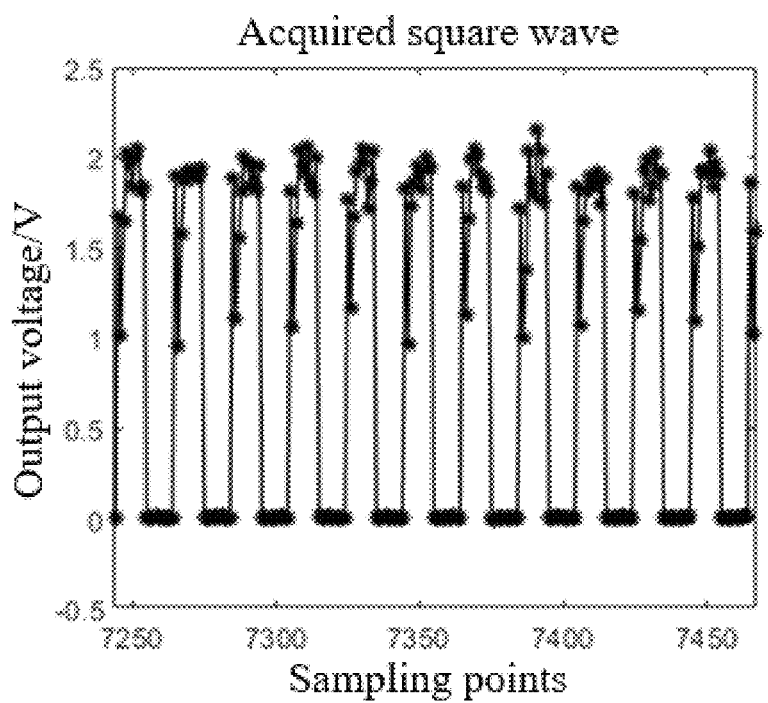
FIG. 12 is a schematic view of an acquired/collected square wave signal according to an embodiment of the disclosure.
Figure 13:
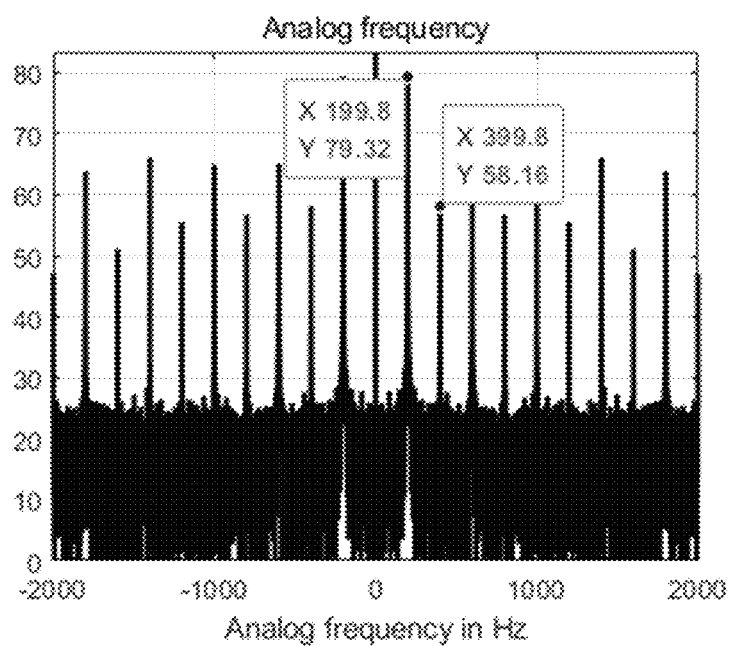
FIG. 13 is a schematic view of a fast Fourier transform of a signal according to an embodiment of the disclosure.
Figure 14:
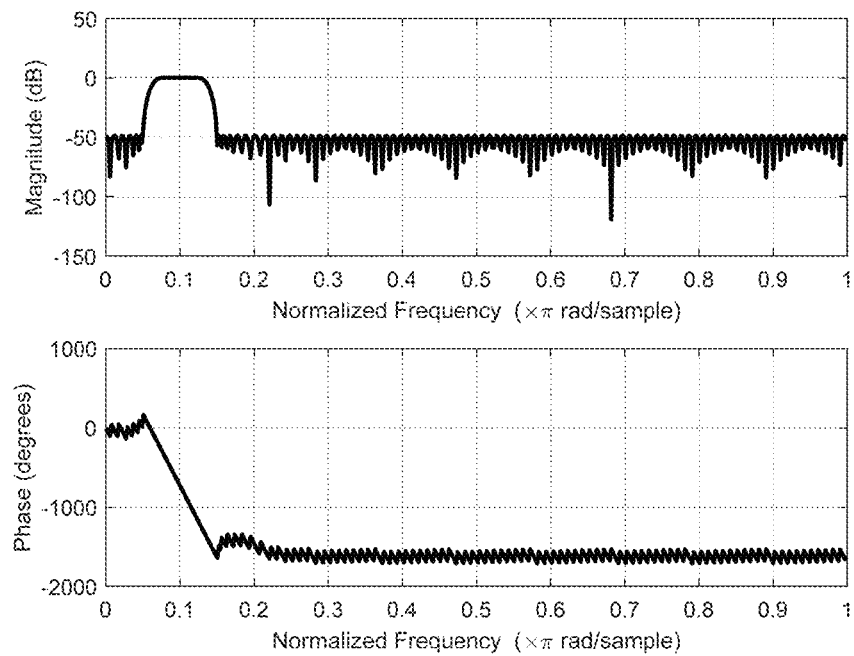
FIG. 14 is a schematic view of an amplitude-frequency characteristic curve of a band-pass filter according to an embodiment of the disclosure.
Figure 15:
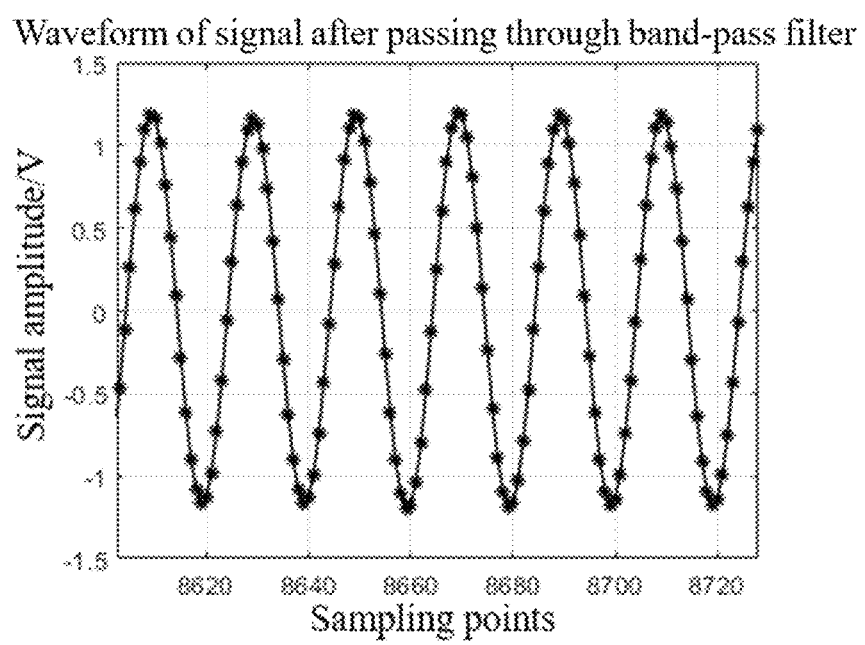
FIG. 15 is a schematic waveform view of a signal after passing through a band-pass filter according to an embodiment of the disclosure.

When the light emitters each are a LED, the frequency of the modulated signal is for example 200 Hz. A data acquisition card with a sampling frequency of 4 KHz is used to collect the signal detected by SiPMs, and finally the square wave signal is obtained as shown in FIG. 12. The square wave is formed by a superposition of a fundamental wave and harmonic waves of different frequencies. When the light emitters are LEDs, only the fundamental wave needs to be retained while the harmonic waves need to be filtered out. All the silicon photomultipliers in the illustrated embodiment are connected in parallel and then connected to the band-pass filter, and the band-pass filter can filter out the harmonic waves while retain the fundamental wave. Referring to FIG. 13, in an absence of the band-pass filter, when observing the frequency spectrum after fast Fourier transform of the signal, there are multiple harmonic components can be found. After the band-pass filter is set/configured, an amplitude-frequency curve of the band-pass filter is shown in FIG. 14, for example, the fundamental signal of 200 Hz is retained and the fundamental signal is shown in FIG. 15, and by extracting the amplitude of the signal, it can be used to reconstruct an absorption coefficient.

Figure 16:
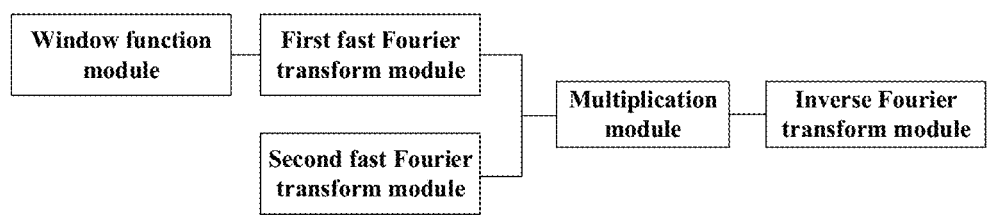
FIG. 16 is a schematic view of a band-pass filter according to an embodiment of the disclosure.

Referring FIG. 16, specifically, the band-pass filter includes a window function module, a first fast Fourier transform module, a second fast Fourier transform module, a multiplication module and an inverse Fourier transform module. The window function module is connected with/to the first fast Fourier transform module. The detector is connected with the second fast Fourier transform module. The first fast Fourier transform module and the second fast Fourier transform module are together connected with the multiplication module, and the multiplication module is connected with the inverse Fourier transform module. The window function module is used to provide a window function. The first fast Fourier transform module is used to perform a Fourier transform on the window function to thereby obtain a first group/set of values. The second fast Fourier transform module is used to perform a Fourier transform on the electrical signal provided by the detector to obtain a second group/set of values. The multiplication module is used to multiply the first group of values and the second group of values to get a third group/set of values. The inverse Fourier transform module is used to perform an inverse Fourier transform on the third group of values to thereby obtain the filtered signal. It can be understood that the band-pass filter includes a processor and a memory connected to the processor, and the memory includes software modules, executable by the processor, such as the window function module, the first fast Fourier transform module, the second fast Fourier transform module, the multiplication module and the inverse Fourier transform module.

In the illustrated embodiment, the window function module is used to provide the window function, so that the last retained waveform is a waveform of a required frequency such as 200 Hz, and therefore only the signal of a limited frequency can be retained by the window function module while the signals of other frequencies are removed. The first fast Fourier transform module can perform a Fourier transform on the window function provided by the window function module to obtain the first group of values, the second fast Fourier transform module can perform a Fourier transform on the electrical signal provided by the detector to obtain the second group of values. In this situation, the number of values in the first group of values and the number of values in the second group of values are the same. Then, the multiplication module can be used to multiply the first group of values and the second group of values one by one, so as to get the third group of values. That is, a first value in the first group of values and a first value in the second group of values are multiplied to get a first value in the third group of values, a second value in the first group of values is multiplied by a second value in the second group of values to get a second value in the third group of values, a third value in the first group of values is multiplied by a third value in the second group of values to get a third value in the third group of values, and so on. After getting the third group of values, an inverse Fourier transform is performed by using the inverse Fourier transform module to thereby obtain the filtered signal, and the filtered signal is a signal being filtered out the harmonic waves and retaining the fundamental wave.

Figure 17:
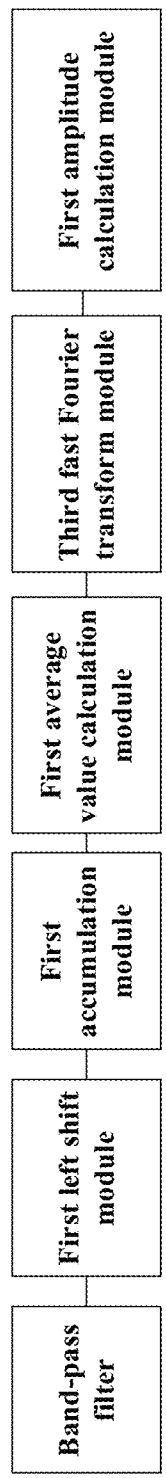
FIG. 17 is a schematic view of an amplitude module according to an embodiment of the disclosure.

The diffusion optical tomography system of the illustrated embodiment further includes an amplitude module (also referred to as amplitude obtainer). The amplitude module is used to obtain an amplitude according to the filtered signal, and the amplitude can be used to obtain the absorption coefficient, thereby reconstructing the image. Referring to FIG. 17, the amplitude module is connected with the inverse Fourier transform module in the band-pass filter. The amplitude module includes a first left shift module, a first accumulation module, a first average value calculation module, a third fast Fourier transform module and a first amplitude calculation module. The inverse Fourier transform module, the first left shift module, the first accumulation module, the first average value calculation module, the third fast Fourier transform module and the first amplitude calculation module are sequentially connected in that order. The first left shift module is used to shift the filtered signal (according to a preset/predetermined method) to obtain a plurality of first shift signals. The first accumulation module is used to accumulate the filtered signal and the plurality of first shift signals to obtain a first accumulated signal. The first average value calculation module is used to obtain a first average signal according to the first accumulated signal and a length of the filtered signal. The third fast Fourier transform module is used to perform a Fourier transform on the first average signal to obtain a fourth group/set of values. The first amplitude calculation module is used to obtain a first preset value in the fourth group of values and obtain an amplitude according to a real part and an imaginary part of the first preset value. It can be understood that the amplitude module (amplitude obtainer) includes a processor and a memory connected to the processor, and the memory includes software modules, executable by the processor, such as the first left shift module, the first accumulation module, the first average value calculation module, the third fast Fourier transform module and the first amplitude calculation module.

In the illustrated embodiment, the first left shift module needs to perform a shift processing on the filtered signal according to the preset method. For example, if the signal length is N, firstly the whole filtered signal is shifted one bit to the left to thereby obtain the first one of the first shift signals, and then the whole filtered signal is shifted two bits to the left to thereby obtain the second one of the first shift signals, until the whole filtered signal is shifted N bits to the left to thereby obtain the N-th one of the first shift signals. After the whole filtered signal is shifted N bits to the left to obtain the N-th one of the first shift signals, signals at corresponding positions of the filtered signal and the first one through the N-th one of the first shift signals are superposed, that is, first bit signals of the filtered signal and the first one through the N-th one of the first shift signals are superposed to obtain a first bit signal of the first accumulation signal, second bit signals of the filtered signal and the first one through the N-th one of the first shift signals are superposed to obtain a second bit signal of the first accumulation signal, and so on, a final first accumulation signal is obtained consequently. For example, if the filtered signal is x={1, 2, 3, 4, 5, 6}, then:

shifting zero bit to the left: x (0)=1 2 3 4 5 6;
shifting one bit to the left: x (1)=2 3 4 5 6 1;
shifting two bits to the left: x (2)=3 4 5 6 1 2;

shifting three bits to the left: x (3)=4 5 6 1 2 3;
shifting four bits to the left: x (4)=5 6 1 2 3 4;
shifting five bits to the left: x (5)=6 1 2 3 4 5; and
shifting six bits to the left: x (6)=1 2 3 4 5 6.

As a result, for the first accumulation signal, the first bit signal thereof is 1+2+3+4+5+6+1=22, the second bit signal thereof is 2+3+4+5+6+1+2=22, the third bit signal thereof is 3+4+5+6+1+2+3=22, the fourth bit signal thereof is 4+5+6+1+2+3+4=22, the fifth bit signal thereof is 5+6+1+2+3+4+5=22, and the sixth bit signal thereof is 6+1+2+3+4+5+6=22. In the illustrated embodiment, after the first accumulation signal is obtained, the first average signal can be calculated out by using the first average value calculation module, that is, the obtained first accumulated signal is divided by the length of the filtered signal to obtain the first average signal. Afterwards, the third fast Fourier transform module can perform a Fourier transform processing on the first average signal to obtain the fourth group/set of values. The first amplitude calculation module can select the first preset value from the fourth group of values. The first preset value is a point corresponding to the required frequency, such as the point corresponding to the frequency of 200 Hz or 25 MHz, and the value corresponding to the point is the first preset value. After the first preset value is obtained, the first amplitude calculation can calculate a square of the real part of the first preset value and a square of the imaginary part of the first preset value under square root, and the calculation result is the required amplitude, which can be used to reconstruct the absorption coefficient and obtain the reconstructed image. The calculation formula of amplitude is as follows:

$$F=\sqrt{a^2+b^2};$$

where F is the amplitude, a is the real part, and b is the imaginary part.

The diffusion optical tomography system provided by the illustrated embodiment of the disclosure has a simple structure and is easy to integrate. The diffusion optical tomography system associated with the disclosure can ensure the stability of signal by using the square wave to modulate the light emitters.

Fourth Embodiment

Detailed description of the diffusion optical tomography system with LDs as the light emitters will be given in an illustrated embodiment, on the basis of the second embodiment.

Figure 18:
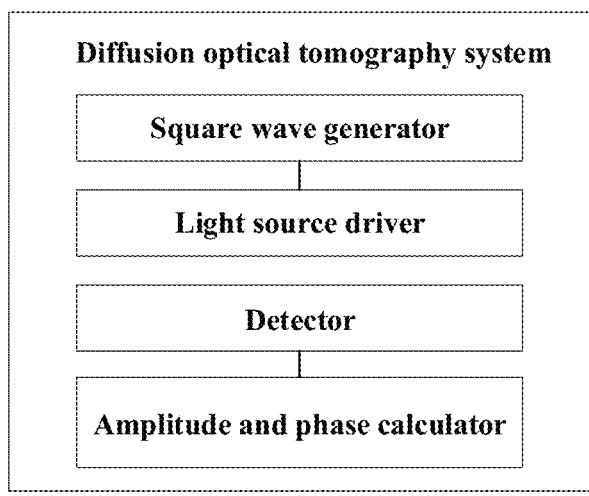
FIG. 18 is a schematic view of another diffusion optical tomography system according to an embodiment of the disclosure.
Figure 19:
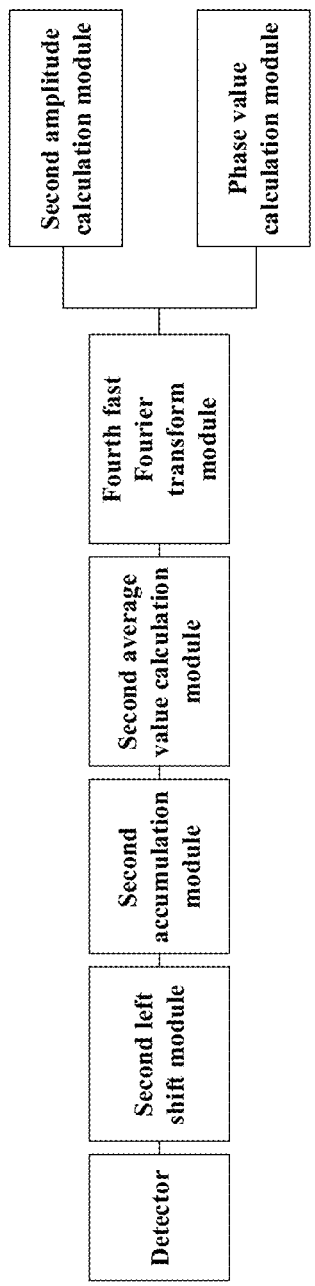
FIG. 19 is a schematic view of an amplitude and phase calculator according to an embodiment of the disclosure.

FIG. 18 is a schematic view of another diffusion optical tomography system provided by an embodiment of the disclosure. When the light emitters each are the LD, the diffusion optical tomography system may further include an amplitude and phase calculator. The amplitude and phase calculator are connected to the detector, that is, all silicon photomultipliers are connected in parallel to the amplitude and phase calculator. Referring FIG. 19, the amplitude and phase calculator includes a second left shift module, a second accumulation module, a second average value calculation module, a fourth fast Fourier transform module, a second amplitude calculation module and a phase calculation module. The detector, the second left shift module, the second accumulation module, the second average value calculation module and the fourth fast Fourier transform module are sequentially connected in that order. The second amplitude calculation module and the phase calculation module are individually connected to the fourth fast Fourier transform module. The second left shift module is used to shift the electrical signal outputted by the detector (according to a preset method) to obtain a plurality of second shift signals. The second accumulation module is used to accumulate the electrical signal and the plurality of second shift signals to obtain a second accumulation signal. The second average value calculation module is used to obtain a second average signal according to the second accumulation signal and a bit number of the electrical signal. The fourth fast Fourier transform module is used to perform a Fourier transform on the second average signal to obtain a fifth group/set of values. The second amplitude calculation module is used to obtain a second preset value in the fifth group of values, and then get an amplitude according to the real part and the imaginary part of the second preset value. The phase calculation module is used to obtain the second preset value in the fifth group of values, and then get a phase according to the real part and the imaginary part of the second preset value. It can be understood that the amplitude and phase calculator includes a processor and a memory connected to the processor, and the memory includes software modules, executable by the processor, such as the second left shift module, the second accumulation module, the second average value calculation module, the fourth fast Fourier transform module, the second amplitude calculation module and the phase calculation module.

In the illustrated embodiment, the second left shift module is used to shift the electrical signal outputted by the detector according to the preset method, for example, if the signal length is N, firstly the whole electrical signal is shifted one bit to the left to obtain a first one of the second shift signals, and then the whole electrical signal is shifted two bits to the left to obtain a second one of the second shift signals, until the whole electrical signal is shifted N bits to the left to obtain an N-th one of the second shift signals. After the whole electrical signal is shifted N bits to the left to obtain the N-th one of the second shift signals, signals at corresponding positions of the electrical signal and the first one through the N-th one of the second shift signals are superposed. That is, first bit signals of the electrical signal and the first one through the N-th one of the second shift signals are superposed to obtain a first bit signal of the second accumulation signal, second bit signals of the electrical signal and the first one through the N-th one of the second shift signals are superposed to obtain a second bit signal of the second accumulation signal, and so on, a final second accumulation signal is obtained consequently.

In the illustrated embodiment, after the second accumulation signal is obtained, the second average signal can be calculated out by using the second average value calculation module, that is, the second average signal is obtained by dividing the second accumulation signal by a length of the electrical signal. Afterwards, the fourth fast Fourier transform module can carry out a Fourier transform processing on the second average signal to obtain the fifth group/set of values. The second amplitude calculation module can select the second preset value from the fifth group of values, the second preset value is the point corresponding to the required frequency, for example, the point corresponding to the frequency of 200 Hz or 25 MHz, and the corresponding value of the point is the second preset value. After the second preset value is obtained, the second amplitude calculation module can calculate a square of the real part of the second preset value and a square of the imaginary part of the second preset value under square root, the calculation result is the required amplitude, which can be used to reconstruct the absorption coefficient and obtain the reconstructed image. The calculation formula of amplitude is as follows:

$$F=\sqrt{a^2+b^2};$$

where F is the amplitude, a is the real part, and b is the imaginary part.

In addition, the phase calculation module can also select the second preset value from the fifth group of values as obtained. After obtaining the second preset value, a phase value can be obtained according to an arctangent value of a ratio of the real part and the imaginary part of the second preset value. A phase difference can be obtained according to the phase value as obtained, and the phase difference can be obtained by a difference between phase values of two signals, for example, the illustrated embodiment employs 56 number of silicon photomultipliers, the phase values of 55 silicon photomultipliers can be respectively subtracted by the remaining one silicon photomultiplier, thus obtaining phase differences corresponding to 55 number of silicon photomultipliers. The amplitude and the phase differences obtained in the illustrated embodiment can be used to reconstruct an absorption coefficient and a scattering coefficient, thereby realizing the reconstruction of image.

The diffusion optical tomography system provided by the illustrated embodiment of the disclosure has a simple structure and is easy to integrate. The diffusion optical tomography system associated with the disclosure can ensure the stability of signal by using the square wave to modulate the light emitters.

Figure 20:
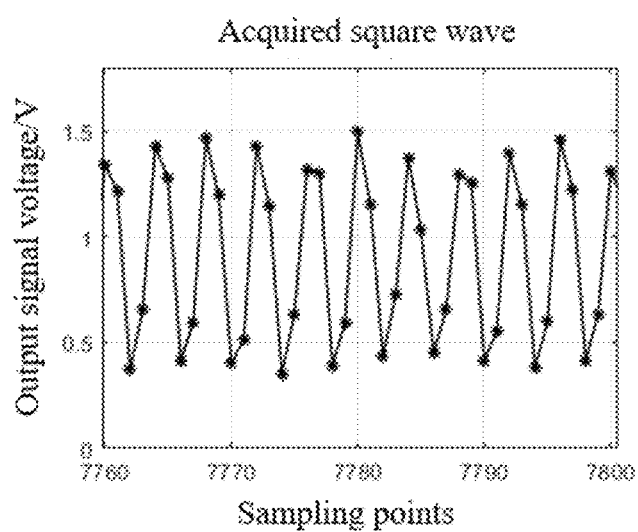
FIG. 20 is a schematic view of another collected square wave signal according to an embodiment of the disclosure.
Figure 21:
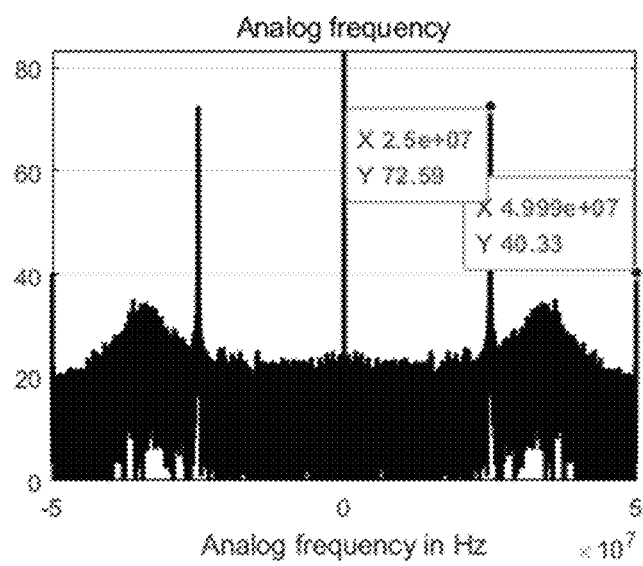
FIG. 21 is a schematic view of a fast Fourier transform of another signal according to an embodiment of the disclosure.

In a frequency-domain operation/working mode, the square-wave generator can generate for example a high-frequency of 25 MHz signal to drive laser diodes, and the signal detected by SiPMs can be sampled by using an acquisition card with an acquisition/sampling frequency of 100 MHz, and the signal waveform is shown in FIG. 20. The frequency spectrum can be observed by performing a fast Fourier transform on the sampled signal, as shown in FIG. 21, and it is found that only 25 MHz fundamental wave signal is basically retained. The calculations of the amplitude and the phase differences of signals can be used to reconstruct the absorption coefficient and the scattering coefficient.

Figure 22:
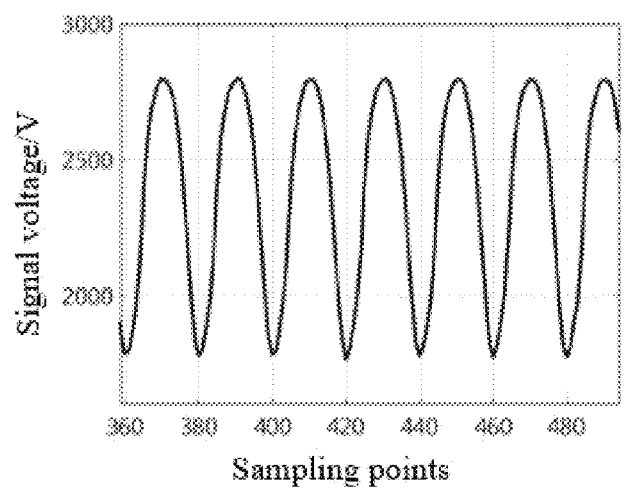
FIG. 22 is a schematic view of output values of SiPM when a modulated signal is a sine wave signal according to an embodiment of the disclosure.
Figure 23:
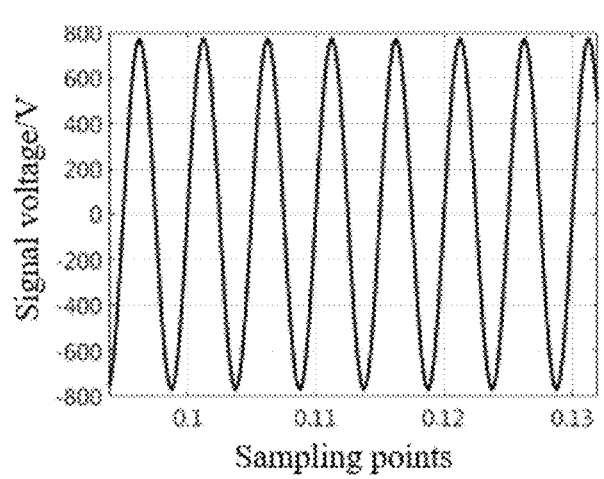
FIG. 23 is a schematic view of output values of SiPM after passing through a band-pass filter when a modulated signal is a square wave signal according to an embodiment of the disclosure.

FIG. 22 is an output value of SiPM when the modulated signal is sine wave, and FIG. 23 is an output value of SiPM after passing through the band-pass filter when the modulated signal is square wave. The illustrated embodiment of the disclosure uses the same light source and the same SiPM based detector, applies a sine wave signal and a square wave signal with the same amplitude and same frequency individually onto the light source, and compares voltage values of output signals of SiPM based detector. After calculation, it is found that the amplitude of the square wave signal is 775.80 mV, and the amplitude of the sine wave signal is 510.05 mV. Therefore, the square wave signal can improve the amplitude of signal and improve the signal-noise ratio.

The illustrated embodiment of the disclosure uses a high-speed acquisition card with a frequency of 100 MHz to directly sample the signal so as to avoid the instability of signal caused by frequency-mixing, and can recover/restore the phase value of the signal better.

TABLE 1

Comparison table of square wave modulation and sine wave modulation.

| | sine wave | square wave |
|---|---|---|
| Integrated circuit | relatively difficult | relatively easy |
| System structure | complex | simple |
| Signal amplitude | relatively small | relatively large |

The diffusion optical tomography system can reduce the system complexity. The system cost can be reduced by using silicon photomultipliers as the detector, and the illustrated embodiment of the disclosure makes full use of the low-pass filtering characteristic of the photodetector SiPM and converts its disadvantages into advantages.

Fifth Embodiment

Figure 24:
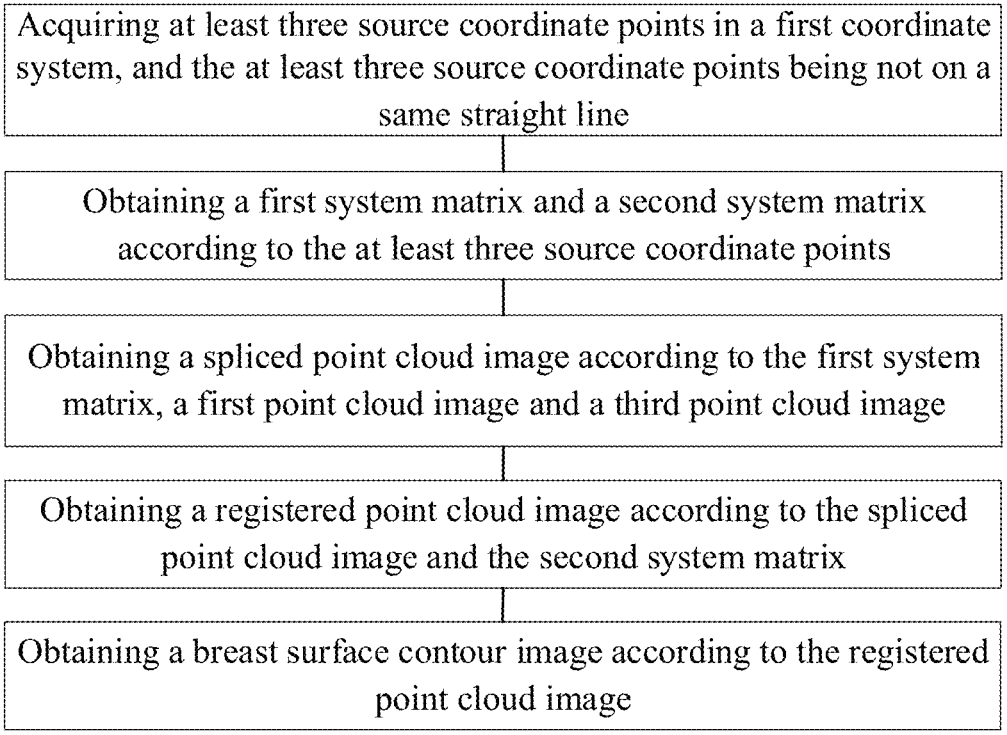
FIG. 24 is a schematic flowchart of a method for obtaining a breast surface contour according to an embodiment of the disclosure.

A method for obtaining a breast surface contour is provided in an illustrated embodiment. Referring to FIG. 24, FIG. 24 is a flowchart of a method for obtaining a breast surface contour provided by an embodiment of the disclosure. Based on the first embodiment, the method for obtaining a breast surface contour provided in the illustrated embodiment uses/adopts the breast diffusion optical tomography device described in the first embodiment for imaging. The method for obtaining a breast surface contour can specifically include steps S1-S5 as follows.

S1, acquiring at least three source coordinate points in a first coordinate system, and the at least three source coordinate points being not on a same straight line;

S2, obtaining a first system matrix and a second system matrix according to the at least three source coordinate points;

S3, obtaining a spliced point cloud image according to the first system matrix, a first point cloud image and a third point cloud image;

S4, obtaining a registered point cloud image according to the spliced point cloud image and the second system matrix; and S5, obtain a breast surface contour according to the registered point cloud image.

Figure 25:
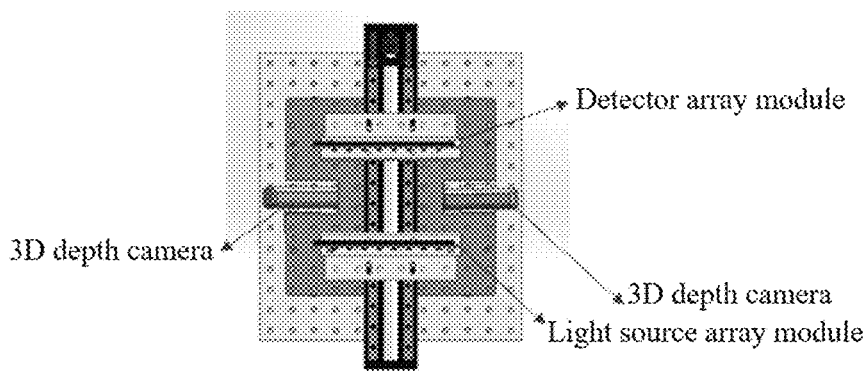
FIG. 25 is a schematic top view of a breast diffusion optical tomography device according to an embodiment of the disclosure.
Figure 26:
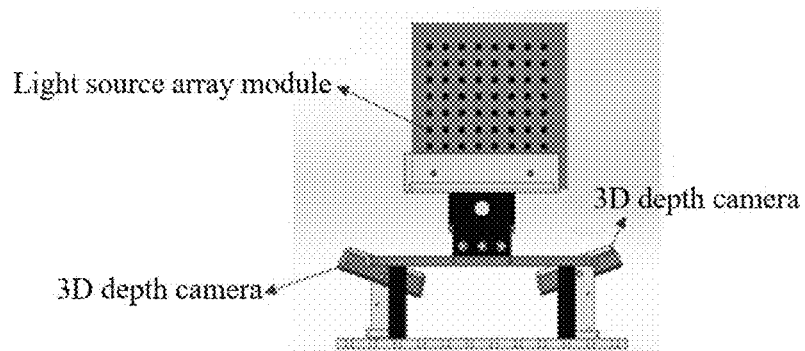
FIG. 26 is a front view of a breast diffusion optical tomography device according to an embodiment of the disclosure.

Referring to FIG. 25 and FIG. 26, FIG. 25 is a top view of a breast diffusion optical tomography device provided by an embodiment of the disclosure, and FIG. 26 is a front view of the breast diffusion optical tomography device provided by an embodiment of the disclosure. In the illustrated embodiment, two three-dimensional (3D) depth cameras are provided on two sides of the breast diffusion optical tomography device respectively. The two 3D depth cameras are arranged between the detector (i.e., detector array module) and the light source (i.e., light source array module), and the two 3D depth cameras are disposed oppositely and respectively located at two sides of the detector as well as the light source. Moreover, the two 3D depth cameras are located under/below the detector as well as the light source. In addition, the two 3D depth cameras are set in a certain elevation angle, so that the breast tissues can be photographed. For example, the angle as set is 45 degrees. In order to facilitate a distance adjustment between the light source and the detector, the detector and the light source can be installed on a slide rail, and the distance between the light source and the detector can be adjusted by moving the light source and the detector on the slide rail.

Specifically, for the step S1, the first coordinate system may be a coordinate system formed by m1 row and n1 column of multi-wavelength light emitters of the light source, the light emitter located at m1-th row and first column can be used as a zero point to establish a coordinate system, and the established coordinate system is the first coordinate system. For example, if the light source includes 7 rows and 8 columns of light emitters, the light emitter located at the seventh row and first column can be used as the zero point to establish a coordinate system. Afterwards, at least three light emitters can be selected as the source coordinate points, and all the selected source coordinate points cannot be on the same horizontal straight line or the same vertical straight line, that is, all the source coordinate points cannot have a same X-axis coordinate value or cannot have a y-axis coordinate value at the same time.

Specifically, for the step S2, it can specifically include sub-steps S21, S22, S22 and S23 as follows.

S21, obtaining first coordinate points according to coordinate values of the source coordinate points in a second coordinate system.

In the illustrated embodiment, the second coordinate system is a coordinate system corresponding to one of the two 3D depth cameras, for example the coordinate system corresponding to the 3D depth camera on the left in FIG. 24. In the embodiment, accessories can be placed on the light emitters corresponding to the selected source coordinate points, as long as they can be distinguished from other light emitters. A point cloud image can be obtained by photographing the light source via the 3D depth camera on the left. The point cloud image will include the light emitters with the accessories and the light emitters without the accessory. Therefore, coordinate positions of the light emitters with the accessories displayed on the point cloud image is coordinate positions of the source coordinate points in the second coordinate system, and the coordinate positions are the first coordinate points.

S22, rotating the first coordinate points around a preset axis of the second coordinate system to a third coordinate system to obtain the first system matrix.

In the illustrated embodiment, the preset axis is y-axis, and the third coordinate system is a coordinate system corresponding to the other one of the two 3D depth cameras, for example, the coordinate system corresponding to the 3D depth camera on the right in FIG. 24. The first system matrix can be obtained by rotating the first coordinate points around the y-axis of the second coordinate system for coordinate transformation matrix, and the first system matrix is as follow:

$$\begin{bmatrix} x' \\ y' \\ z' \\ 1 \end{bmatrix} = \begin{bmatrix} \cos\theta_1 & 0 & \sin\theta_1 & t_{x_1} \\ 0 & 1 & 0 & 0 \\ -\sin\theta_1 & 0 & \cos\theta_1 & t_{z_1} \\ 0 & 0 & 0 & 1 \end{bmatrix} \begin{bmatrix} x_1 \\ y_1 \\ z_1 \\ 1 \end{bmatrix};$$

where $x_1$, $y_1$ and $z_1$ represent coordinates of the first coordinate points, $t_{x_1}$ is an offset along the x-axis of the second coordinate system, $t_{z_1}$ is an offset along the z-axis of the second coordinate system, $\cos\theta_1$ is a rotation angle around the y-axis of the second coordinate system, and x', y' and z' are coordinates of the first coordinate points transformed to the third coordinate system.

S23, obtaining second coordinate points according to coordinate positions of the source coordinate points in the third coordinate system.

In the illustrated embodiment, the second coordinate points are coordinate points corresponding to x', y' and z' obtained from the first system matrix.

S24, rotating the second coordinate points around a preset axis of the third coordinate system to the first coordinate system to obtain the second system matrix.

In the illustrated embodiment, the preset axis is y-axis, and the second system matrix can be obtained by rotating the second coordinate points around the y-axis of the third coordinate system for coordinate transformation matrix, and the second system matrix is as follow:

$$\begin{bmatrix} x'' \\ y'' \\ z'' \\ 1 \end{bmatrix} = \begin{bmatrix} \cos\theta_2 & 0 & \sin\theta_2 & t_{x_2} \\ 0 & 1 & 0 & 0 \\ -\sin\theta_2 & 0 & \cos\theta_2 & t_{z_2} \\ 0 & 0 & 0 & 1 \end{bmatrix} \begin{bmatrix} x' \\ y' \\ z' \\ 1 \end{bmatrix};$$

where $t_{x_2}$ is an offset along the x-axis of the third coordinate system, $t_{z_2}$ is an offset along the z-axis of the third coordinate system, $\theta_2$ is a rotation angle around the y-axis of the third coordinate system, and x'', y'' and z'' are coordinates of the second coordinate points transformed to the first coordinate system.

Specifically, for the step S3, it may specifically include sub-steps S31 through S33 as follows.

S31, acquiring coordinate values of first points in the first point cloud image.

In the illustrated embodiment, breast tissues are clamped between the detector and the light source. A point cloud image is obtained by photographing the breast tissues by the 3D depth camera corresponding to the second coordinate system. The point cloud image is the first point cloud image, and the first points are points captured/photographed and displayed in the first cloud image.

S32, obtaining a second point cloud image according to coordinate values of the first points and the first system matrix.

In the illustrated embodiment, the second point cloud image can be obtained by multiplying the coordinate values of all the first points with the first system matrix, so that the first points corresponding to the second coordinate system can be transformed to the third coordinate system.

S33, obtaining the spliced point cloud image according to the third point cloud image and the second point cloud image.

Figure 27:
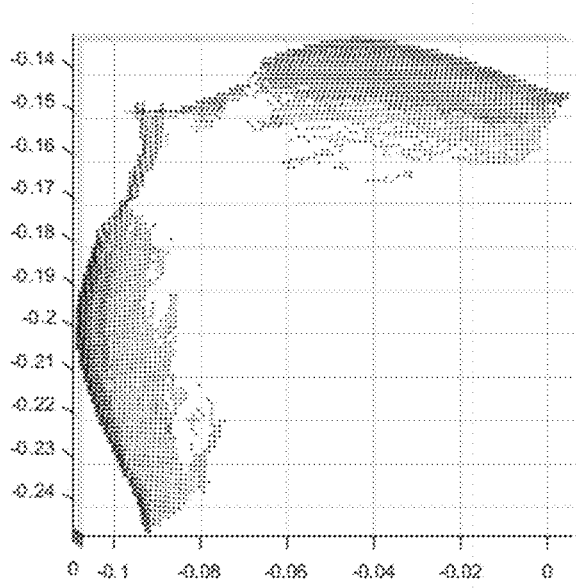
FIG. 27 is a schematic view of a spliced point cloud image according to an embodiment of the disclosure.

In the illustrated embodiment, the 3D depth camera corresponding to the third coordinate system captures the breast tissues to obtain a point cloud image, which is the third point cloud image. The spliced point cloud image can be obtained by splicing the third point cloud image and the second point cloud image together. For example, FIG. 27 is a kind of spliced point cloud image.

Specifically, for the step S4, it may specifically include sub-steps S41 and S42 as follows.

S41, acquiring coordinate values of second points in the spliced point cloud image.

In the illustrated embodiment, the spliced point cloud image includes a plurality of points, and the plurality of points in the spliced point cloud image are the second points.

S42, obtaining the registered point cloud image according to the coordinate values of the second points and the second system matrix.

Figure 28:
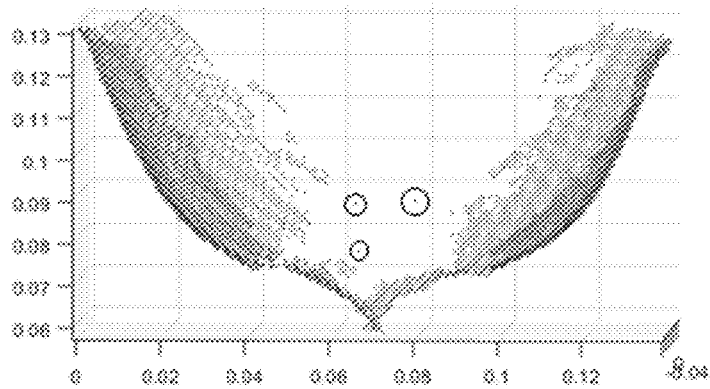
FIG. 28 is a schematic view of a registered point cloud image according to an embodiment of the disclosure.

In the illustrated embodiment, the registered point cloud image can be obtained by multiplying coordinate values of all the second points with the second system matrix, so that the second points corresponding to the third coordinate system can be transformed to the first coordinate system. For example, FIG. 28 is a registered point cloud image obtained by the spliced point cloud image of FIG. 27.

Specifically, for the step S5, it may specifically include sub-steps S51 through S53 as follows.

S51, performing a surface fitting processing on the registered point cloud image to obtain a fitting image.

Figure 29:
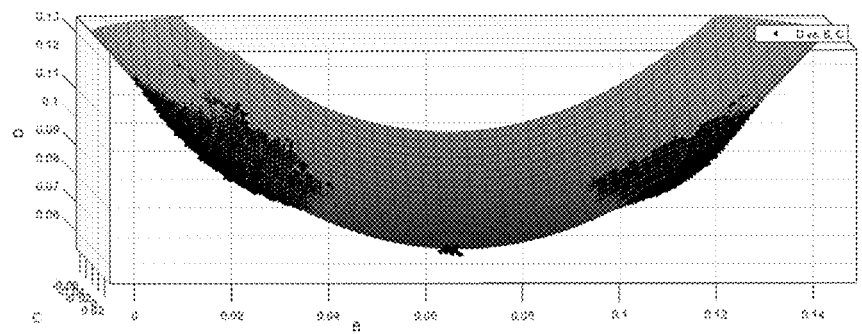
FIG. 29 is a schematic view of a fitting image according to an embodiment of the disclosure.

In the illustrated embodiment, the fitting image is obtained by surface fitting of the registered point cloud image by using MATLAB, for example, a least square method is used to fit the registered point cloud image to thereby obtain the fitting image. For example, FIG. 29 is a fitting image obtained by the registered point cloud image in FIG. 28. The surface equation corresponding to the fitting image is: $z=0.1299-1.866x+0.4891y+13.34x^2+0.6324xy+13.06y^2$, where x, y and z represent coordinate values respectively.

S52, obtaining a closed contour point cloud image by performing a point sampling and a point cloud complement processing on the fitting image.

Figure 30:
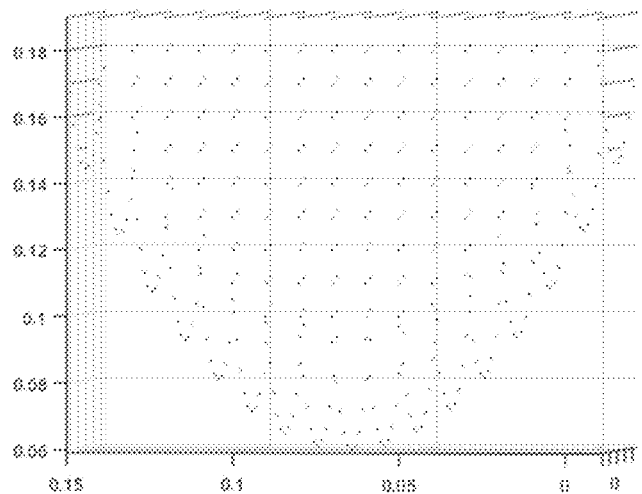
FIG. 30 is a schematic view of a contour point cloud image according to an embodiment of the disclosure.
Figure 31:
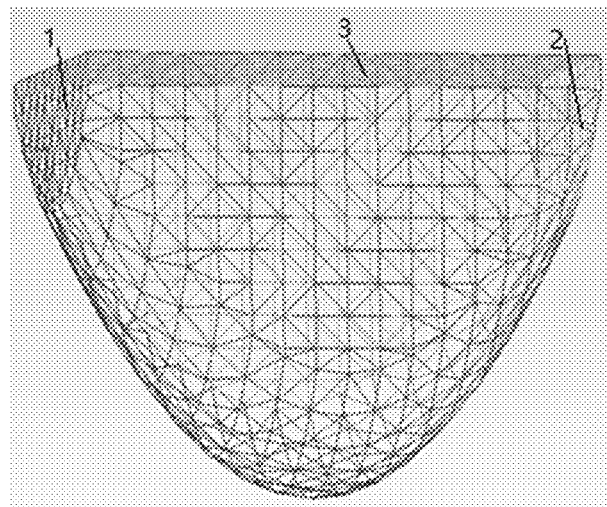
FIG. 31 is a schematic view of a surface contour according to an embodiment of the disclosure.

In the illustrated embodiment, the point sampling is performed on the fitting image, for example, the sampling is performed by taking one point every preset distance, and the preset distance is 1 mm. Because when placing breast tissues between detector array module and the light source array module, it will be squeezed, so the squeezed positions of the breast tissues during shooting/photographing are missing surfaces, and meanwhile a top surface of the breast tissues also is a missing surface. After point/dot sampling the fitting image to obtain a sampled image, the missing surfaces in the sampled image needs to be supplemented by point cloud filling to thereby obtain the closed contour point cloud image. For example, FIG. 30 is a contour point cloud image obtained by the fitting image of FIG. 29, and reference signs of 1, 2 and 3 shown in FIG. 31 are the missing surfaces.

S53, obtaining the breast surface contour according to the closed contour point cloud image. The sub-step S53 may include the following S531 and S532.

S531, performing a surface contour mesh construction processing on the closed contour point cloud image to obtain a surface contour image by using a triangular finite element method.

In the illustrated embodiment, it is required to perform the surface contour mesh construction on the closed contour point cloud image, and more specifically, the obtained closed contour point cloud image is carried out with the surface contour mesh construction by the triangular finite element method. For example, FIG. 31 is a surface contour image obtained by the contour point cloud image of FIG. 30.

S532, obtaining the breast surface contour by performing a mesh generation processing on the surface contour image.

Figure 32:
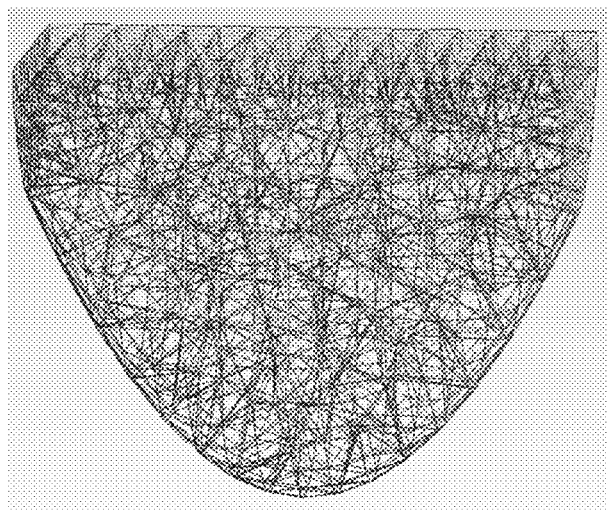
FIG. 32 is a schematic view of a breast surface contour according to an embodiment of the disclosure.

In the illustrated embodiment, a mesh generation method is used to carry out a mesh generation processing on the surface contour image, so that the breast surface contour image can be obtained. For example, FIG. 32 is a breast surface contour image obtained by the contour point cloud image of FIG. 31.

An accuracy verification of the method for obtaining a surface contour associated with the embodiment is as follow.

In order to ensure the accuracies of the system matrices, a Euclidean distance between the coordinate value obtained by the system matrix and the actual coordinate value is taken as the error of the matrix. The error measurement selects three coordinate points for calculation, and an average value of three groups of measurement results is taken as the final error value. In an alternative embodiment, a plurality of groups of data can be selected for calculation, so as to improve accuracy and reliability of results. The calculation formula is as follows:

$$h = \frac{1}{n}\sum_{i=1}^{n} \sqrt{(x_{it}-x_{im})^2 + (y_{it}-y_{im})^2 + (z_{it}-z_{im})^2} \; ;$$

where h represents the error value, n represents the number of selected source coordinate points, a subscript it represents an actual coordinate value of the source coordinate point, and a subscript im represents a coordinate value of the source coordinate point calculated by the system matrix.

TABLE 2

| accuracy test of the first system matrix | | | | | | | | |
|---|---|---|---|---|---|---|---|---|
| Unit (mm) | $X_{it}$ | $Y_{it}$ | $Z_{it}$ | $X_{im}$ | $Y_{im}$ | $Z_{im}$ | Error | Mean value |
| No.1 source coordinate point | −41.75 | −8.95 | −199.70 | −42.03 | −9.12 | −200.50 | 0.86 | 1.12 |
| No.2 source coordinate point | 6.38 | 29.48 | −156.50 | 5.95 | 30.28 | −155.42 | 1.41 | |
| No.3 source coordinate point | −4.13 | −32.41 | −159.50 | −4.23 | −33.26 | −160.20 | 1.10 | |

TABLE 3

| accuracy test of the second system matrix | | | | | | | | |
|---|---|---|---|---|---|---|---|---|
| Unit (mm) | $X_{it}$ | $Y_{it}$ | $Z_{it}$ | $X_{im}$ | $Y_{im}$ | $Z_{im}$ | Error | Mean value |
| No.1 source coordinate point | 75.13 | 40.26 | 85.14 | 76.24 | 40.35 | 85.37 | 1.14 | 1.10 |
| No.2 source coordinate point | 63.41 | 40.28 | 85.76 | 63.74 | 40.26 | 84.63 | 1.17 | |
| No.3 source coordinate point | 63.43 | 40.25 | 73.15 | 62.45 | 40.32 | 73.27 | 0.99 | |

Through the above tests, it can be concluded that the error of coordinate value calculated by the system matrix is 1~2 mm, because the required accuracy of image reconstruction is within 5 mm, and thus it will not have a significant impact on the quality of the image. Therefore, the method for obtaining a surface contour of the illustrated embodiment can meet the requirement of reconstruction.

The illustrated embodiment of the disclosure adopts the solution/scheme of synchronously collecting contours by dual-sided three-dimensional depth cameras, which can ensure accurate acquisition of the morphological features of the breast, and can provide reliable data for the final image reconstruction and quantification of optical parameters in the tissues to complete the work.

The disclosure can solve the technical problem of quickly and accurately obtaining the contour of the breast surface contour in limited space and field of view without rotating, in a specific scene of a flat panel system. In a case of similar application scenarios where the acquisition of morphological features of tissues is limited by space and field of view, the solution proposed by the disclosure can be used to obtain the surface contour of the breast.

In the description of the disclosure, terms such as "first" and "second" are used for descriptive purposes only, and cannot be understood as indicating or implying relative importance or implicitly indicating the number of indicated technical features. Thus, the features defined with "first" and "second" can explicitly or implicitly include one or more of these features. In the description of the disclosure, "a plurality of" or "multiple" means two or more, unless otherwise specifically defined.

In the description of this specification, descriptions with reference to the terms such as "an embodiment", "some embodiments", "examples", "specific examples", or "some examples" mean that the specific feature(s), structure(s), material(s), or characteristic(s) described in conjunction with the embodiment or example is/are included in at least one embodiment or example of the disclosure. In the specification, the schematic expressions/representations of the above terms do not necessarily refer to the same embodiment or example. Moreover, the described specific feature(s), structure(s), material(s) or characteristic(s) as described may be combined in a suitable manner in any one or more embodiments or examples. In addition, those skilled in the art may join and combine different embodiments or examples described in the specification.

The above content is a detailed description of the disclosure in combination with specific preferred embodiment, and it cannot be considered that the specific implementations of the disclosure are limited to these descriptions. For those of ordinary shill in the technical field to which the disclosure belongs, a number of simple deductions or substitutions can be made without departing from the concept of the disclosure, and they should all be regarded as belonging to the protection scope of the disclosure.

What is claimed is:

1. A breast diffusion optical tomography device comprising: a light source, a detector and an acquisitor;
   wherein the light source and the detector are movable along a predetermined direction;
   wherein the light source comprises a continuous-wave mode light source and a frequency-domain mode light source, the detector comprises a continuous-wave mode detector and a frequency-domain mode detector, and the acquisitor comprises a continuous-wave mode acquisitor and a frequency-domain mode acquisitor;
   wherein the continuous-wave mode light source comprises M1 number of multi-wavelength light emitters for a continuous-wave mode, and the frequency-domain mode light source comprises M2 number of laser diodes of different wavelengths for a frequency-domain mode, and M2 is less than M1; the continuous-wave mode detector comprises N1 number of silicon photomultipliers for a detection in the continuous-wave mode, and the frequency-domain mode detector comprises N2 number of silicon photomultipliers for a detection in the frequency-domain mode; and the N2 number of silicon photomultipliers are some of the N1 number of silicon photomultipliers, and N2 is less than N1; and
   wherein an arrangement of the M1 number of multi-wavelength light emitters, an arrangement of the M2 number of laser diodes, an arrangement of the N1 number of silicon photomultipliers and an arrangement of the N2 number of silicon photomultipliers each are a uniform spacing arrangement, the N1 number of silicon photomultipliers are connected to the continuous-wave mode acquisitor, and the N2 number of silicon photomultipliers are connected to the frequency-domain mode acquisitor;
   wherein the M1 number of multi-wavelength light emitters comprise m1 rows and n1 columns of multi-wavelength light emitters for the continuous-wave mode, and the M2 number of laser diodes comprise m2 rows and n2 columns of laser diodes of different wavelengths for the frequency-domain mode, m2 is less than m1, and n2 is less than n1; each row of the m2 rows of laser diodes is arranged between adjacent two rows of the m1 rows of multi-wavelength light emitters; the N1 number of silicon photomultipliers comprise m1 rows and n1 columns of silicon photomultipliers; the m1 rows and n1 columns of silicon photomultipliers and the m1 rows and n1 columns of multi-wavelength light emitters are opposite to each other and are arranged in a one-to-one correspondence manner, N2, m1, n1, m2 and n2 each are an integer greater than 1.

2. The breast diffusion optical tomography device according to claim 1, further comprising: a light source switcher;
   wherein the light source switcher comprises a plurality of first analog switches, a second analog switch, a plurality of first decoders and a second decoder;
   wherein a plurality of first output terminals of the continuous-wave mode acquisitor are correspondingly connected to a plurality of first input terminals of each of the plurality of first analog switches and a plurality of first input terminals of the second analog switch, a plurality of second output terminals of the continuous-wave mode acquisitor are correspondingly connected to a plurality of input terminals of each of the plurality of first decoders, and a plurality of third output terminals of the continuous-wave mode acquisitor are correspondingly connected to a plurality of input terminals of the second decoder;
   wherein each of output terminals of the second decoder is connected to an enable terminal of one of the plurality of first decoders, one of output terminals of each of the plurality of first decoders is connected to an enable terminal of one of the plurality of first analog switches, a plurality of output terminals of each of the plurality of first analog switches are correspondingly connected to light emitters of a same wavelength in a same row of the M1 number of multi-wavelength light emitters, and one output terminal of one of the plurality of first decoders is connected to an enable terminal of the second analog switch.

3. The breast diffusion optical tomography device according to claim 2, further comprising: a driving circuit;
wherein the driving circuit comprises a first capacitor (C1), a first resistor (R1), a second resistor (R2), a transistor (Q) and a plurality of third resistors (R3);
wherein an analog output terminal of the continuous-wave mode acquisitor is connected to a first terminal of the first resistor (R1), a first terminal of the second resistor (R2) and a base electrode of the transistor (Q) through the first capacitor (C1); a second terminal of the first resistance (R1) is connected to a grounding terminal, an emitter electrode of the transistor (Q) is connected to the grounding terminal, a collector electrode of the transistor (Q) is connected to second input terminals of the plurality of first analog switches and a second input terminal of the second analog switch;
wherein the output terminals of each of the plurality of first analog switches are connected to cathodes of the light emitters of the same wavelength in the same row of the M1 number of multi-wavelength light emitters through the third resistors (R3) respectively, each output terminal of the second analog switch is connected to a cathode of one of the M2 number of laser diodes through the third resistor (R3), and anodes of the light emitters and anodes of the laser diodes are together connected to a second terminal of the second resistor (R2) and a power supply terminal.

4. The breast diffusion optical tomography device according to claim 1, wherein the light source comprises a plate-shaped structure, and the detector comprises a plate-shaped structure; and the plate-shaped structure of the light source and the plate-shaped structure of the detector are arranged in parallel.

5. The breast diffusion optical tomography device according to claim 4, further comprising: a plurality of temperature sensors;
wherein the plurality of temperature sensors are arranged on the plate-shaped structure and connected to the continuous-wave mode acquisitor.

6. The breast diffusion optical tomography device according to claim 4, further comprising: a mechanical driver;
wherein the mechanical driver comprises two sliders, a screw rod, a slide rail and a motor;
wherein the light source and the detector are respectively arranged on the sliders, the screw rod passes through screw holes of the two sliders, and an end of the screw rod is connected to the motor; and
wherein the screw rod is a singular piece and comprises a first screw rod part and a second screw rod part, spiral directions of the first screw rod part and the second screw rod part are opposite to each other, the first screw rod part passes through the screw hole of one of the sliders arranged with the light source and connects with an end of the second screw rod part, the other end of the second screw rod part passes through the screw hole of the other of the sliders arranged with the detector and connects with the motor, and bottom ends of the sliders are arranged on the slide rail.

7. A diffusion optical tomography system based on square wave modulation, comprising the breast diffusion optical tomography device according to claim 1; wherein the diffusion optical tomography system further comprises:
a square-wave generator, configured to obtain a square wave according to a sine wave; and
a light source driver, connected to the square-wave generator and configured to apply the square wave to the light emitters of the light source and thereby drive the light emitters to emit light beams for irradiating an object to be measured;
wherein the detector is configured to detect an optical signal generated by the light beams emitted from the light emitters passing through the object to be measured and convert the optical signal into an electrical signal.

8. The diffusion optical tomography system according to claim 7, wherein the square-wave generator comprises a microcontroller unit (MCU), a direct digital synthesizer (DDS), a comparison module, a direct current (DC) voltage source and an addition module; the MCU is connected to the DDS, the DDS is connected to the comparison module, and the comparison module and the DC voltage source are connected to the addition module;
wherein the DDS is configured to generate the sine wave according to a control of the MCU;
wherein the comparison module is configured to obtain a first square wave according to the sine wave; and
wherein the addition module is configured to obtain a second square wave according to a voltage amplitude of the first square wave and a DC voltage provided by the DC voltage source, and a voltage amplitude of the second square wave is a positive voltage.

9. The diffusion optical tomography system according to claim 8, wherein the light source driver comprises a second capacitor (C2), a fourth resistor (R4), a fifth resistor (R5), a sixth resistor (R6), (M1+M2) number of light emitters, a transistor (Q1) and a DC power supply;
wherein a first terminal of the second capacitor (C2) is connected to the addition module, a second terminal of the second capacitor (C2) is connected to a first terminal of the fourth resistor (R4) and a base electrode of the transistor (Q1), the sixth resistor (R6) is connected in series between an emitter electrode of the transistor (Q1) and an grounding terminal, a second terminal of the fourth resistor (R4) is connected to a first terminal of the fifth resistor (R5) and a positive electrode of the DC power supply, anodes of the (M1+M2) number of light emitters are together connected to a second terminal of the fifth resistor (R5), cathodes of the (M1+M2) number of light emitters are together connected to a collector electrode of the transistor (Q1), and a negative electrode of the DC power supply is connected between the sixth resistor (R6) and the grounding terminal.

10. The diffusion optical tomography system according to claim 9, wherein the detector comprises a plurality of silicon photomultipliers, and the light emitters comprise light-emitting diodes (LEDs).

11. The diffusion optical tomography system according to claim 10, further comprising: a band-pass filter;
wherein the band-pass filter is connected to the detector and configured to filter out harmonic waves in the second square wave and retain a fundamental wave in the second square wave to thereby obtain a filtered signal.

12. The diffusion optical tomography system according to claim 11, wherein the band-pass filter comprises software modules including a window function module, a first fast Fourier transform module, a second fast Fourier transform module, a multiplication module and an inverse Fourier transform module; and the software module are stored in a memory and executable by a processor connected to the memory;
wherein the window function module is connected to the first fast Fourier transform module, the detector is connected to the second fast Fourier transform module, the first fast Fourier transform module and the second fast Fourier transform module are connected to the multiplication module, and the multiplication module is connected to the inverse Fourier transform module;

wherein the window function module is configured to provide a window function;

wherein the first fast Fourier transform module is configured to perform a Fourier transform on the window function to obtain a first set of values;

wherein the second fast Fourier transform module is configured to perform a Fourier transform on the electrical signal provided by the detector to obtain a second set of values;

wherein the multiplication module is configured to multiply the first set of values with the second set of values to obtain a third set of values; and wherein the inverse Fourier transform module is configured to perform an inverse Fourier transform on the third set of values to obtain the filtered signal.

13. The diffusion optical tomography system according to claim 12, further comprising: an amplitude obtainer, connected to the band-pass filter;

wherein the amplitude obtainer comprises software modules including a first left shift module, a first accumulation module, a first average value calculation module, a third fast Fourier transform module and a first amplitude calculation module; and the software modules are stored in a memory and executable by a processor connected to the memory;

wherein the first left shift module is connected to the band-pass filter and configured to perform a shift processing on the filtered signal to obtain a plurality of first shift signals;

wherein the first accumulation module is connected to the first left shift module and configured to accumulating the filtered signal and the plurality of first shift signals to obtain a first accumulation signal;

wherein the first average value calculation module is connected to the first accumulation module and configured to obtain a first average signal according to the first accumulation signal and a length of the filtered signal;

wherein the third fast Fourier transform module is connected to the first average value calculation and configured to perform a Fourier transform on the first average signal to obtain a fourth set of values; and wherein the first amplitude calculation module is connected to the third fast Fourier transform module and configured to obtain a first preset value from the fourth set of values and then obtain an amplitude according to a real part and an imaginary part of the first preset value.

14. The diffusion optical tomography system according to claim 9, further comprising: an amplitude and phase calculator, connected to the detector;

wherein the amplitude and phase calculator comprises software module including a second left shift module, a second accumulation module, a second average value calculation module, a fourth fast Fourier transform module, a second amplitude calculation module, and a phase calculation module; and the software modules are stored in a memory and executable by a processor connected to the memory;

wherein the second left shift module is connected to the detector and configured to perform a shift processing on the electrical signal outputted by the detector to obtain a plurality of second shift signals;

wherein the second accumulation module is connected to the second left shift module and configured to accumulate the electrical signal and the plurality of second shift signals to obtain a second accumulation signal;

wherein the second average value calculation module is connected to the second accumulation module and configured to obtain a second average signal according to the second accumulation signal and a bit number of the electrical signal;

wherein the fourth fast Fourier transform module is connected to the second average value calculation module and configured to perform a Fourier transform on the second average signal to obtain a fifth set of values;

wherein the second amplitude calculation module is connected to the fourth fast Fourier transform module and configured to obtain a second preset value from the fifth set of values and then obtain an amplitude according to a real part and an imaginary part of the second preset value;

wherein the phase calculation module is connected to the fourth fast Fourier transform module and configured to obtain the second preset value from the fifth set of values and then obtain a phase value according to the real part and the imaginary part of the second preset value; and wherein the light emitters comprise laser diodes (LDs).

15. The breast diffusion optical tomography device according to claim 4, further comprising: a light source switcher;

wherein the light source switcher comprises a plurality of first analog switches, a second analog switch, a plurality of first decoders and a second decoder;

wherein a plurality of first output terminals of the continuous-wave mode acquisitor are correspondingly connected to a plurality of first input terminals of each of the plurality of first analog switches and a plurality of first input terminals of the second analog switch, a plurality of second output terminals of the continuous-wave mode acquisitor are correspondingly connected to a plurality of input terminals of each of the plurality of first decoders, and a plurality of third output terminals of the continuous-wave mode acquisitor are correspondingly connected to a plurality of input terminals of the second decoder;

wherein each of output terminals of the second decoder is connected to an enable terminal of one of the plurality of first decoders, one of output terminals of each of the plurality of first decoders is connected to an enable terminal of one of the plurality of first analog switches, a plurality of output terminals of each of the plurality of first analog switches are correspondingly connected to light emitters of a same wavelength in a same row of the Ml number of multi-wavelength light emitters, and one output terminal of one of the plurality of first decoders is connected to an enable terminal of the second analog switch.

16. The breast diffusion optical tomography device according to claim 15, further comprising: a driving circuit;

wherein the driving circuit comprises a first capacitor (C1), a first resistor (R1), a second resistor (R2), a transistor (Q) and a plurality of third resistors (R3);

wherein an analog output terminal of the continuous-wave mode acquisitor is connected to a first terminal of the first resistor (R1), a first terminal of the second resistor (R2) and a base electrode of the transistor (Q) through the first capacitor (C1); a second terminal of the first resistance (R1) is connected to a grounding terminal, an emitter electrode of the transistor (Q) is connected to the grounding terminal, a collector electrode of the transistor (Q) is connected to second input terminals of the plurality of first analog switches and a second input terminal of the second analog switch;

wherein the output terminals of each of the plurality of first analog switches are connected to cathodes of the light emitters of the same wavelength in the same row of the M1 number of multi-wavelength light emitters through the third resistors (R3) respectively, each output terminal of the second analog switch is connected to a cathode of one of the M2 number of laser diodes through the third resistor (R3), and anodes of the light emitters and anodes of the laser diodes are together connected to a second terminal of the second resistor (R2) and a power supply terminal.

17. The breast diffusion optical tomography device according to claim 1, wherein for the N2 number of silicon photomultipliers, each row of the silicon photomultipliers is between adjacent two rows of the laser diodes.

18. The breast diffusion optical tomography device according to claim 15, wherein for the m1 rows and n1 columns of multi-wavelength light emitters, each the multi-wavelength light emitter is composed of N number of light emitters with different wavelengths.

19. The breast diffusion optical tomography device according to claim 18, wherein the each of the plurality of first analog switches is configured to control light emitters in a same wavelength in a same row, and the first analog switches configured to control the light emitters in the same wavelength in the same row of the plurality of first analog switches are connected to a same first detector of the plurality of first detectors; and the second analog switch is configured to control the m2 rows and n2 columns of laser diodes.

20. The breast diffusion optical tomography device according to claim 6, wherein the first screw rod part and the second screw rod part are configured to rotate to drive the two sliders to move in opposite directions respectively, so that the light source and the detector respectively arranged on the two sliders move in opposite directions, and thereby adjusting a spacing between the light source and the detector.

* * * * *